United States Patent
Knell et al.

(10) Patent No.: US 10,737,046 B2
(45) Date of Patent: *Aug. 11, 2020

(54) INHALER

(71) Applicant: Boehringer Ingelheim Vetmedica GmbH, Ingelheim am Rhein (DE)

(72) Inventors: Marcus Knell, Ingelheim (DE); Guido Endert, Leichlingen (DE); Horst Wergen, Essen (DE)

(73) Assignee: BOEHRINGER INGELHEIM VETMEDICA GMBH, Ingelheim am Rhein (DE)

(*) Notice: Subject to any disclaimer, the term of this patent is extended or adjusted under 35 U.S.C. 154(b) by 335 days.

This patent is subject to a terminal disclaimer.

(21) Appl. No.: 15/889,515

(22) Filed: Feb. 6, 2018

(65) Prior Publication Data
US 2018/0161528 A1    Jun. 14, 2018

Related U.S. Application Data

(63) Continuation of application No. 14/462,867, filed on Aug. 19, 2014, now Pat. No. 9,913,952.

(30) Foreign Application Priority Data

Aug. 20, 2013  (EP) .................................. 13004114

(51) Int. Cl.
*A61M 15/08*    (2006.01)
*A61D 7/04*    (2006.01)
(Continued)

(52) U.S. Cl.
CPC ............... *A61M 15/08* (2013.01); *A61D 7/04* (2013.01); *A61M 11/006* (2014.02); *A61M 15/009* (2013.01); *A61M 15/0013* (2014.02); *A61M 15/0073* (2014.02); *A61M 15/0086* (2013.01); *A61M 15/0093* (2014.02);
(Continued)

(58) Field of Classification Search
CPC ............... A61M 15/08; A61M 11/006; A61M 15/0013; A61M 15/0073; A61M 15/0093; A61M 15/0096; A61M 15/0086; A61M 15/009; A61M 15/0018; A61M 2205/581;
(Continued)

(56) References Cited

U.S. PATENT DOCUMENTS 4,470,412 A    9/1984  Nowacki et al.
4,534,343 A    8/1985  Nowacki et al.
(Continued)

FOREIGN PATENT DOCUMENTS

AU        620375 B2    8/1990
CA    2 653 422 A1    12/2007
(Continued)

*Primary Examiner* — Timothy A Stanis
*Assistant Examiner* — Jonathan S Paciorek
(74) *Attorney, Agent, or Firm* — David S. Safran; Roberts Calderon Safran & Cole, P.C.

(57) ABSTRACT

An inhaler with a respiration indicator, whereby the inhaler has a chamber wall forming a chamber and a dispensing device for fluidic connection of the chamber to a bodily opening, preferably a nostril, whereby the respiration indicator has a wall section of the chamber wall or is formed in this way, whereby the wall section is designed to indicate a respiratory activity by deformation and/or movement.

21 Claims, 16 Drawing Sheets

(51) Int. Cl.
*A61M 15/00* (2006.01)
*A61M 11/00* (2006.01)

(52) U.S. Cl.
CPC ..... *A61M 15/0096* (2014.02); *A61M 15/0018* (2014.02); *A61M 2205/581* (2013.01); *A61M 2205/583* (2013.01); *A61M 2250/00* (2013.01)

(58) Field of Classification Search
CPC ........ A61M 2205/583; A61M 2250/00; A61D 7/04
See application file for complete search history.

(56) References Cited

U.S. PATENT DOCUMENTS

| | | | |
|---|---|---|---|
| 4,559,939 A | 12/1985 | Levine et al. | |
| 4,623,337 A | 11/1986 | Maurice | |
| 4,832,015 A | 5/1989 | Nowacki et al. | |
| 5,012,804 A | 5/1991 | Foley et al. | |
| 5,139,171 A | 8/1992 | Mäder | |
| 5,292,033 A | 3/1994 | Gueret | |
| 5,332,121 A | 7/1994 | Schmidt et al. | |
| 5,385,140 A | 1/1995 | Smith | |
| 5,511,538 A | 4/1996 | Haber et al. | |
| 5,645,049 A | 7/1997 | Foley et al. | |
| 5,666,948 A * | 9/1997 | Matson ............... | A61D 7/04 128/200.23 |
| 5,695,125 A | 12/1997 | Kumar | |
| 5,740,794 A | 4/1998 | Smith et al. | |
| 5,743,252 A | 4/1998 | Rubsamen et al. | |
| 5,785,049 A | 7/1998 | Smith et al. | |
| 5,833,088 A | 11/1998 | Kladders et al. | |
| 5,848,588 A | 12/1998 | Foley et al. | |
| 5,878,915 A | 3/1999 | Gordon et al. | |
| 5,954,049 A | 9/1999 | Foley et al. | |
| 5,957,125 A | 9/1999 | Sagstetter et al. | |
| 5,964,416 A | 10/1999 | Jaeger et al. | |
| 6,026,807 A | 2/2000 | Puderbaugh et al. | |
| 6,089,228 A | 7/2000 | Smith et al. | |
| 6,257,233 B1 | 7/2001 | Burr et al. | |
| 6,338,422 B1 | 1/2002 | DeJonge | |
| 6,401,712 B1 | 6/2002 | von Schuckmann | |
| 6,435,177 B1 | 8/2002 | Schmidt et al. | |
| 6,543,448 B1 | 4/2003 | Smith et al. | |
| 6,546,929 B2 | 4/2003 | Burr et al. | |
| 6,644,305 B2 | 11/2003 | MacRae et al. | |
| 6,901,929 B2 | 6/2005 | Burr et al. | |
| 6,988,496 B1 | 1/2006 | Eicher et al. | |
| 7,004,162 B1 | 2/2006 | Foley et al. | |
| 7,056,494 B2 | 6/2006 | Adjei et al. | |
| 7,077,126 B2 | 7/2006 | Kummer et al. | |
| 7,275,534 B2 | 10/2007 | Childers et al. | |
| 7,360,537 B2 | 4/2008 | Snyder et al. | |
| 7,422,013 B2 | 9/2008 | Burr et al. | |
| 7,467,629 B2 | 12/2008 | Rand | |
| 7,571,722 B2 | 8/2009 | Wuttke et al. | |
| 7,717,299 B2 | 5/2010 | Greiner-Perth | |
| 7,726,302 B1 | 6/2010 | Nielsen | |
| 7,779,836 B2 | 8/2010 | Andersson et al. | |
| 8,056,765 B2 | 11/2011 | Auerbach et al. | |
| 8,286,632 B2 | 10/2012 | Rohrschneider et al. | |
| 8,291,854 B2 | 10/2012 | Behnisch et al. | |
| 8,297,277 B2 | 10/2012 | Rohrschneider et al. | |
| 8,550,067 B2 | 10/2013 | Bruce et al. | |
| 8,584,669 B2 | 11/2013 | Bessler et al. | |
| 8,905,020 B2 | 12/2014 | Eagle | |
| 9,067,034 B2 | 6/2015 | Djupesland et al. | |
| 9,156,048 B2 | 10/2015 | Le Maner | |
| 9,265,910 B2 | 2/2016 | Wachtel | |
| 9,352,107 B2 | 5/2016 | Von Hollen et al. | |
| 2002/0017294 A1 | 2/2002 | Py | |
| 2002/0029779 A1 | 3/2002 | Schmidt et al. | |
| 2002/0157664 A1 | 10/2002 | Fugelsang et al. | |
| 2002/0170928 A1 | 11/2002 | Grychowski et al. | |
| 2003/0168058 A1 | 9/2003 | Walker et al. | |
| 2004/0011819 A1 | 1/2004 | Jennings et al. | |
| 2004/0134494 A1 | 7/2004 | Papania et al. | |
| 2004/0250816 A1 | 12/2004 | Kummer et al. | |
| 2005/0016528 A1 | 1/2005 | Aslin et al. | |
| 2005/0034723 A1 | 2/2005 | Bennett et al. | |
| 2005/0183718 A1 | 8/2005 | Wuttke et al. | |
| 2005/0183719 A1 | 8/2005 | Wuttke et al. | |
| 2005/0247305 A1 | 11/2005 | Zierenberg et al. | |
| 2007/0051363 A1 | 3/2007 | Andrus et al. | |
| 2007/0107722 A1 | 5/2007 | Hoelz et al. | |
| 2007/0164049 A1 | 7/2007 | Bonney et al. | |
| 2007/0225645 A1 | 9/2007 | Tarinelli | |
| 2007/0267016 A1 | 11/2007 | Thoemmes et al. | |
| 2008/0135578 A1 | 6/2008 | Ophardt | |
| 2008/0178871 A1 | 7/2008 | Genova et al. | |
| 2008/0272144 A1 | 11/2008 | Bonney et al. | |
| 2009/0107498 A1 | 4/2009 | Plattner et al. | |
| 2010/0258120 A1 | 10/2010 | Columb | |
| 2011/0088690 A1* | 4/2011 | Djupesland ......... | A61M 15/009 128/200.23 |
| 2012/0017900 A1 | 1/2012 | Bacon | |
| 2012/0103326 A1 | 5/2012 | Karle et al. | |
| 2012/0203125 A1 | 8/2012 | Moran | |
| 2012/0318265 A1 | 12/2012 | Amirav et al. | |

FOREIGN PATENT DOCUMENTS

| | | |
|---|---|---|
| EP | 0 134 847 A1 | 3/1985 |
| EP | 0 166 476 A2 | 1/1986 |
| WO | 90/07351 A1 | 7/1990 |

* cited by examiner

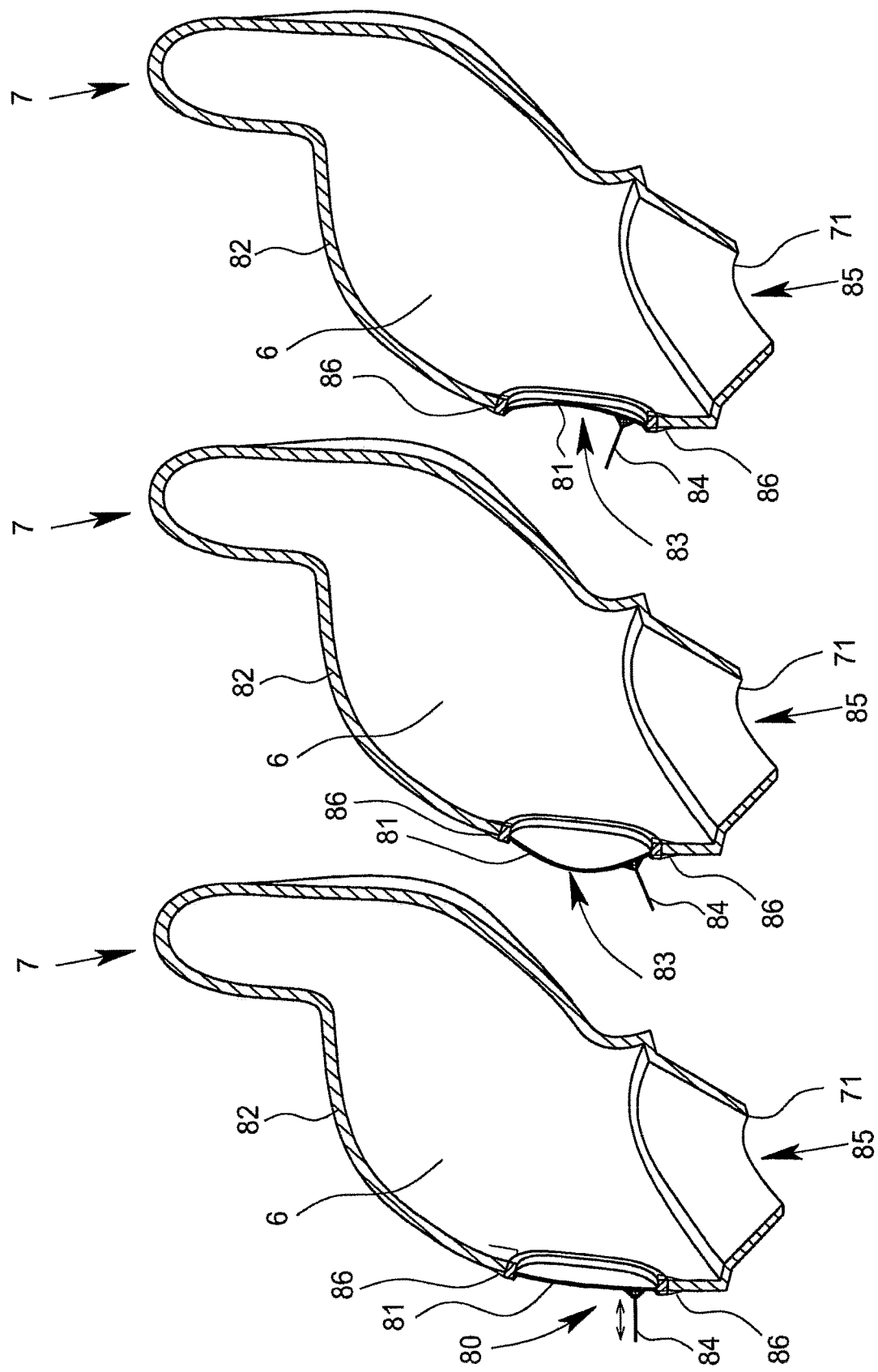

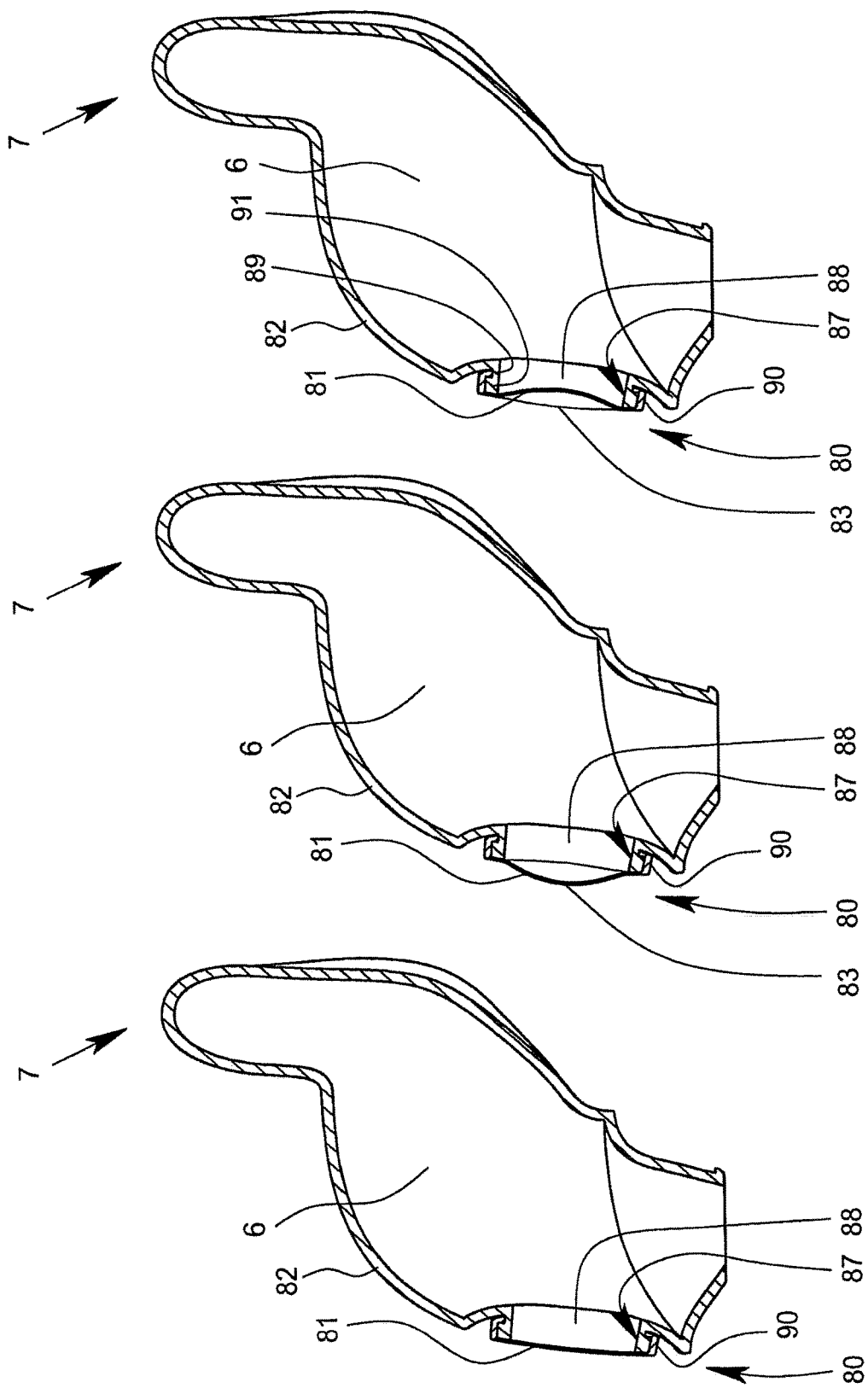

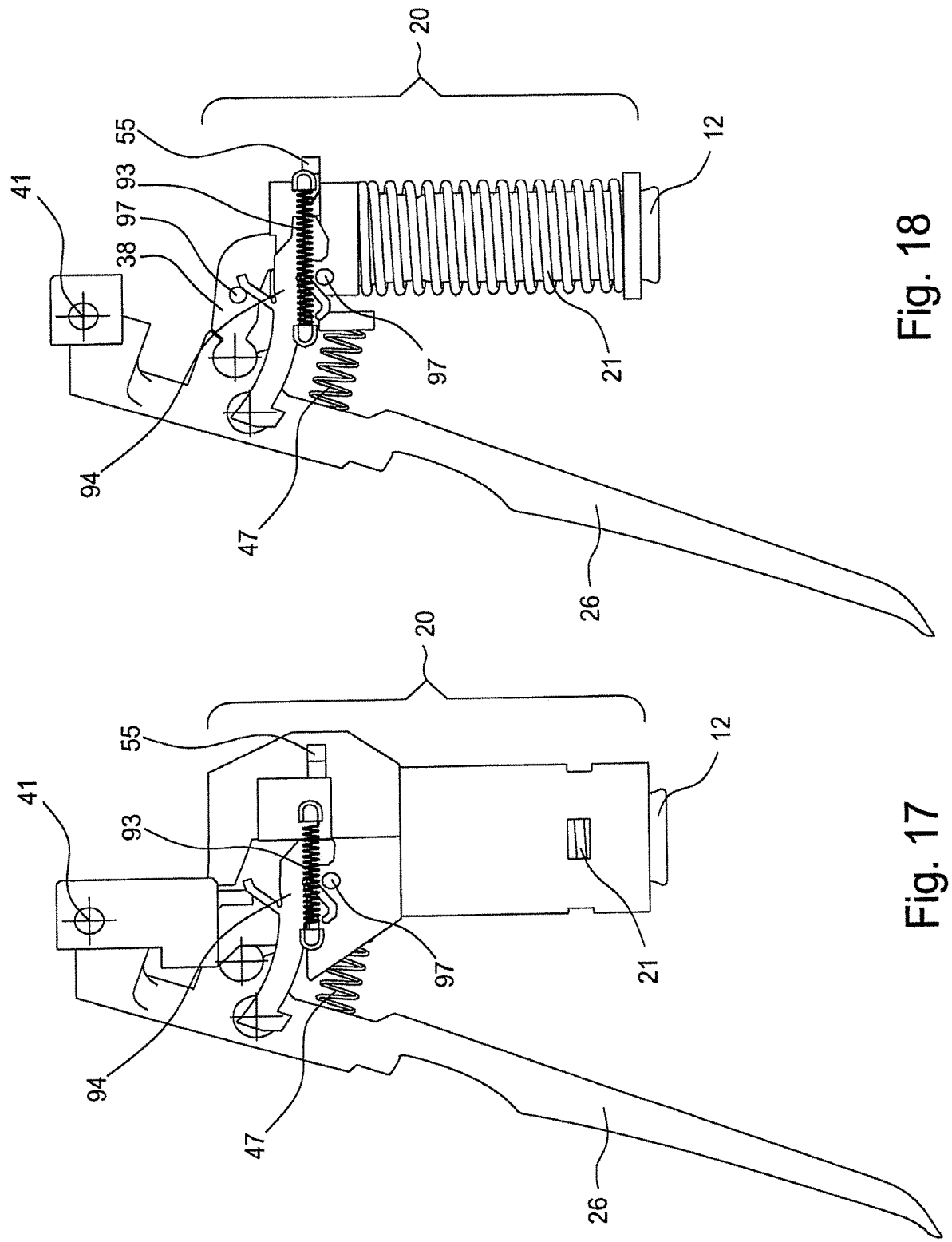

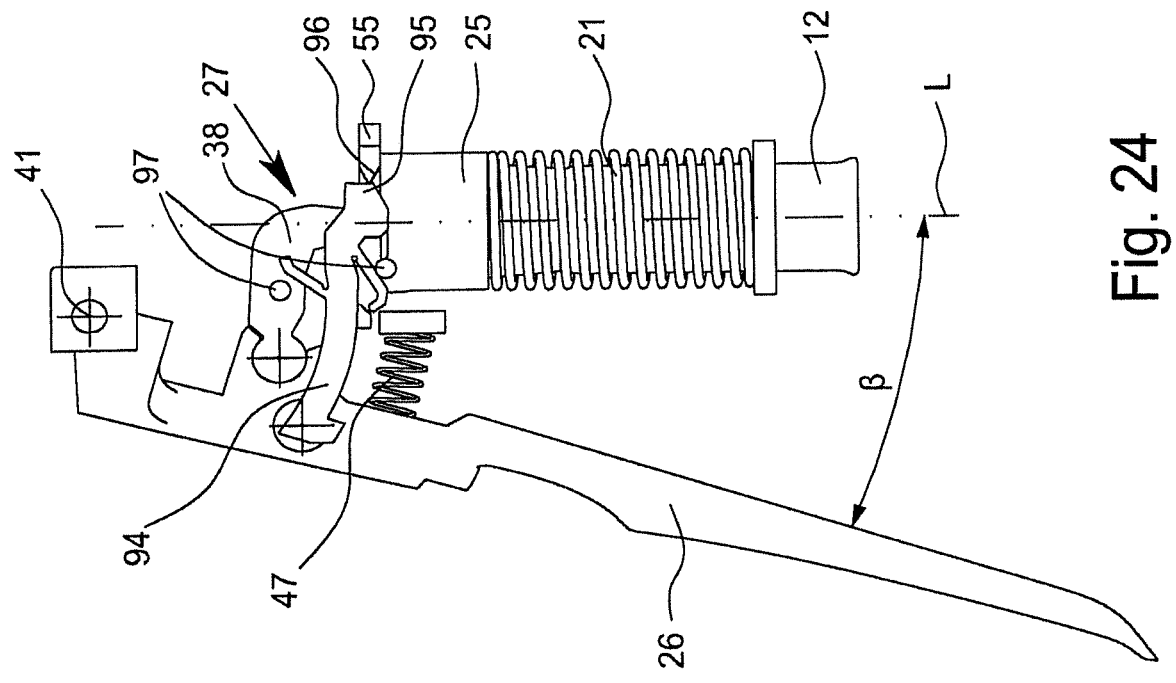
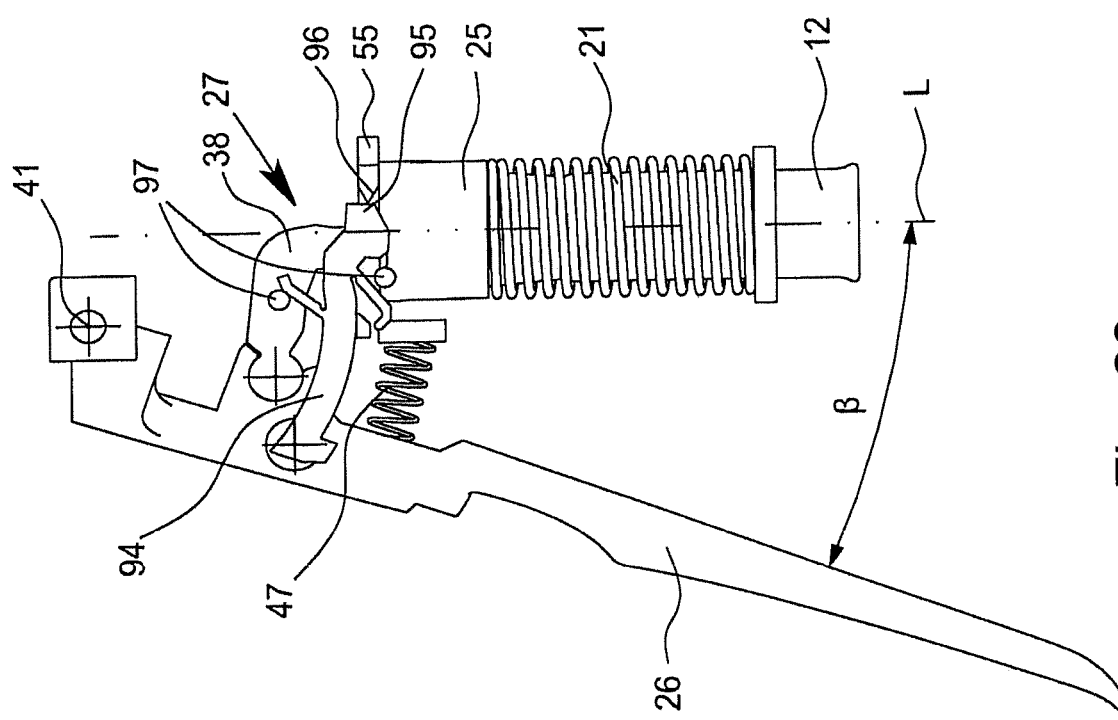

INHALER

CROSS REFERENCE TO RELATED APPLICATION

This application is a continuation of commonly owned, co-pending U.S. patent application Ser. No. 14/462,867, filed Aug. 19, 2014, which claims priority of European Patent Application 13 004 114.8 filed Aug. 20, 2013.

FIELD OF THE INVENTION

This invention relates to an inhaler, preferably for insertion into a nostril, in particular a horse's nostril, with a respiration indicator, whereby the inhaler has a chamber wall forming a chamber and a dispensing device for fluidic connection of the chamber to a body orifice, preferably a nostril, in particular a horse's nostril.

DESCRIPTION OF RELATED ART

This invention relates in particular to a so-called Soft Mist Inhaler (SMI), i.e., an inhaler that produces an atomized spray (aerosol) that propagates only comparatively slowly. In terms of this invention, such inhalers are in particular inhalers in which an aerosol is dispensed at a speed of less than 2 m/s, preferably approximately 1.6 m/s or less, and quite especially preferably less than 1 m/s (in each case measured at a distance of 10 cm from a discharge nozzle) and/or in which the dispensing or spraying of a dose—of preferably 10 to 50 µl of a pharmaceutical agent preparation—lasts longer than 0.7 s, in particular approximately 1 s or longer.

International Patent Application Publication WO 2005/079997 A1 and corresponding U.S. Pat. No. 7,571,722 disclose an inhaler that represents an SMI in terms of this invention. As a reservoir for a pharmaceutical agent preparation that is to be sprayed, the known inhaler has an insertable, rigid container with an inner bag with the pharmaceutical agent preparation and a pressure generator with a mainspring for delivery and spraying of the pharmaceutical agent preparation. The spraying is done without propellant, namely under the action of the force of the mainspring.

Also, the known inhaler has an inhalation valve, which is arranged laterally to a discharge nozzle.

It is problematic in the case of inhalers and even SMIs in general that the triggering of the spraying of the pharmaceutical agent preparation and the inhalation must be coordinated. This can be difficult for the individual user. This tends to be problematic in the case of SMIs because of the relatively long spraying time per dose. Therefore, the SMIs were previously not used for humans with coordination problems, such as small children, and not for animals, in particular large animals, such as horses.

International Patent Application Publication WO 2004/091704 A1 and corresponding U.S. Pat. No. 7,360,537 disclose an additional device for intermediate storage of a sprayed pharmaceutical agent preparation in a chamber, also called a spacer. The additional device is inserted into a so-called Metered Dose Inhaler (MDI). An MDI has a pressurized container that contains the pharmaceutical agent preparation to be sprayed as well as propellant. Upon actuation, the propellant causes the pharmaceutical agent preparation to be dispensed at comparatively high pressure and correspondingly high speed and with a high mass stream. Therefore, the dispensing occurs for only a very short time, in particular for less than 0.4 s, and in most cases for approximately 0.15-0.39 s. The short dispensing time is disadvantageous for an inhalation, since the intake for inhalation usually lasts significantly longer. The comparatively high speed of more than 2 m/s, often even up to or over 8 m/s, with which the aerosol is usually administered by an MDI, is also disadvantageous for uptake into the lungs, since the particles (droplets) of the aerosol are deposited for the most part on the wall of the user's throat because of the high speed in the case of direct inhalation.

The known additional device is provided for an MDI and serves to slow down the aerosol, in particular by lengthening the flow path. For this reason, such additional devices are also called spacers. In addition, the additional device serves to ensure intermediate storage for the aerosol that is produced.

International Patent Application Publication WO 01/78818 A2 and corresponding U.S. Pat. No. 6,644,305 disclose an inhaler for the nose. The inhaler has a pump cylinder that can be actuated manually and an adapter, arranged thereon, with a chamber for intermediate storage of an aerosol that is produced. The pump cylinder is not an SMI in terms of this invention. Rather, a short and strong actuation of the pump cylinder is necessary in order to achieve an acceptable spraying, so that the characteristics correspond to those of an MDI, if, by means of the pump cylinder, an aerosol can be produced at all with the very small droplets desired for inhalation in the lungs.

International Patent Application Publication WO 94/17753 A1 and corresponding U.S. Pat. No. 5,666,948 disclose an inhalation device for large animals, such as horses. The inhalation device comprises an MDI, which releases an aerosol in an additional device with a tubular section. The aerosol is sprayed in the longitudinal direction of the tubular section. A soft adapter can be connected to the tubular section, which adapter is designed for insertion into a horse's nostril. According to a variant embodiment, the inhalation device has a handle with a corresponding, manually actuatable, pivotable actuating element. Upon actuation of the actuating element, the MDI is shifted linearly, ensuring that a metering valve of the MDIs is opened and aerosol is released into the tubular section. In the case of MDIs, it is disadvantageous that the spraying is carried out by propellant. Further, the operation is problematic. The direction in which the actuating element can be actuated manually runs parallel to the longitudinal extension of the tubular section or additional device, so that an operator intuitively positions himself on the side opposite the administration side of the additional device; this is very disadvantageous, however, for the application in the case of a horse when the operator would like to hold the horse at the same time.

International Patent Application Publication WO 2010/149280 and U.S. Patent Application Publication 2012/103326 relate to a Soft Mist Inhaler with an additional device for intermediate storage of a sprayed pharmaceutical agent mixture in a chamber. The additional device has an inhalation valve for intake of incoming air into the chamber and for blocking in the opposite direction. Further, the inhaler has a dispensing device that is connected to the additional device in order to make possible a dispensing of aerosol to a patient to be treated. The inhalation valve is hinged laterally and therefore opens up on one side, which deflects the incoming air stream.

International Patent Application Publication WO 03/097142 A1 relates to an inhaler with a respiration indicator that is arranged to be visible in a window in a channel guided along an adapter of the inhaler. The indicator has a swiveling flap that releases the channel in a basic position, i.e., when there is no respiratory activity, and in the case of inhalation activity is entrained by suctioning air through the channel into the inhaler from the flow that is produced in order to indicate the respiratory activity. While an intake activity is indicated, the flap of the indicator closes the channel, and thus secondary air is pulled in for only a short time. This approach is based on a delicate mechanical-fluidic interaction system, which is susceptible to error by suctioning off substances through the channel or penetration of substances such as respiratory condensates or secretions and furthermore is production-intensive and costly because of the necessary precision.

SUMMARY OF THE INVENTION

The object of this invention is to provide an inhaler, especially preferably an SMI, with which respiratory activity can be reliably indicated even under adverse circumstances.

The above object is achieved by an inhaler as described herein.

The respiration indicator according to the present invention comprises a wall section of the chamber wall or is formed thereby, whereby the wall section is configured to indicate respiratory activity by deformation and/or movement.

The formation of the respiration indicator at least partially by the wall section offers the advantage that at no time is there an additional, lateral air intake necessary. Such an additional air intake can lead to turbulences and deposition of active ingredients. The respiration indicator is also arranged outside of the flow, i.e., also leads here neither to an obstacle, a pressure loss, nor to turbulence formation or results in active ingredient loss owing to deposition, or the like. Another advantage of the respiration indicator according to the invention is its simple and robust design, which works without joints, rotatable parts, or the like. In this way, the respiration indicator is extremely sturdy. The respiration indicator preferably does not have any rotatable parts and can be formed in one piece or can otherwise be free of channels, openings, hollow spaces, and the like. Thus, it is ruled out that foreign substances jeopardize an operability of the respiration indicator under adverse circumstances, for example when used in veterinary medicine.

The above-mentioned aspects and features can be produced independently of one another, but also in any combination.

Other advantages, features, properties, and aspects of this invention will be apparent from the following description with reference to the accompanying drawings.

BRIEF DESCRIPTION OF THE DRAWINGS

FIG. 11 is a sectional view of the chamber with a dispensing device of the inhaler in the area of the respiration indicator in the rest position;

FIG. 12 is a sectional view of the chamber with a dispensing device of the inhaler in the area of the respiration indicator in the expiratory position;

FIG. 13 is a sectional view of the chamber with a dispensing device of the inhaler in the area of the respiration indicator in the inhalation position;

FIG. 14 is a sectional view of the chamber with a dispensing device of the inhaler in the area of the respiration indicator in accordance with an alternative embodiment in the rest position;

FIG. 15 is a sectional view of the chamber with a dispensing device of the inhaler in the area of the respiration indicator in accordance with an alternative embodiment in the expiratory position;

FIG. 16 is a sectional view of the chamber with a dispensing device of the inhaler in the area of the respiration indicator in accordance with an alternative embodiment in the inhalation position;

FIG. 17 is a side view of the inhaler in accordance with a second embodiment of the invention;

FIG. 18 is a side view of the inhaler in accordance with a second embodiment of the invention with the outside shell of the container of the pressure generator removed;

FIG. 23 is a view corresponding to that of FIG. 18 showing the pressure generator in accordance with the second embodiment with an actuating lever in the rest position with a tensioned tensioning device; and FIG. 24 is a view corresponding to that of FIG. 18 showing the pressure generator in accordance with the second embodiment with the actuating lever at the trigger point.

DETAILED DESCRIPTION OF THE INVENTION

In the figures, the same reference numbers are used for identical or similar parts, whereby corresponding or comparable properties and advantages can be achieved even if a description is not repeated.

Figure 1:
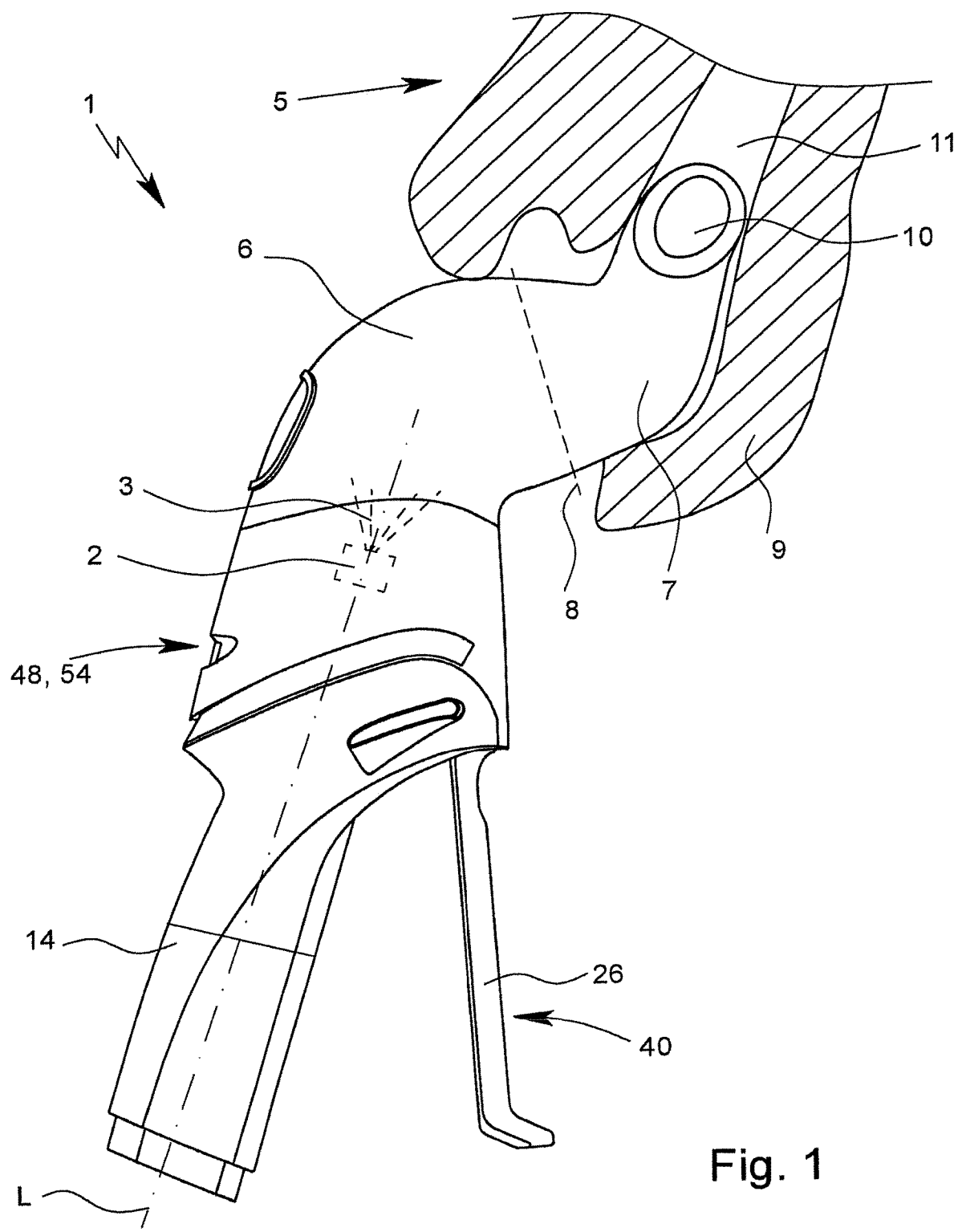
FIG. 1 is a side view of an inhaler according to the invention in a nostril.

FIG. 1 shows a view of an inhaler 1 according to the invention. The inhaler 1 has a discharge nozzle 2 that is indicated in dotted lines in FIG. 1 and that preferably is designed for forming an aerosol 3 with a pharmaceutical agent preparation 4.

When spraying the pharmaceutical agent preparation 4, preferably a liquid, the preferably respirable aerosol 3 is formed, which can be breathed in or inhaled by a user or patient, not shown, such as an animal, a human, or preferably a large animal, in particular a horse 5. Usually, the inhalation is done at least once daily, in particular several times daily, preferably at predetermined time intervals, in particular based on the disease.

The inhaler 1 preferably has a dispensing device 7 for fluidic connection of the chamber 6 to a bodily orifice, preferably a nostril 9, in particular the nostril of a horse 5. The dispensing device 7 is preferably formed in one piece with the chamber 6 or is connected to the latter.

The aerosol 3 can be intermediately stored in a chamber 6 and/or administered by the dispensing device 7.

The chamber 6 is preferably designed for uptake and/or intermediate storage of the aerosol 3 that is realized by the inhaler 1. The chamber 6 is preferably arranged or can be arranged downstream from the discharge nozzle 2. The chamber 6 can be designed at least partially in a tubular, cylindrical, elongated or conical manner.

In the illustrated embodiment, the introduction of the aerosol 3 into the chamber 6 is done in the spraying direction of the discharge nozzle 2, along a lengthwise extension of the inhaler 1, or in the direction of flow in the area of the discharge nozzle 2, or axially or in the direction of the longitudinal axis L.

The chamber 6 and the dispensing device 7 can be formed separately or in multiple pieces, for example by a connection in the area of the connecting line 8 indicated in dotted lines. In the illustrated embodiment, the chamber 6 is formed in one piece with the dispensing device 7, in particular an adapter for a body orifice, in particular a nose or nostril 9. In this way, recesses and gaps, to which contaminants can adhere or into which they can enter, can be avoided.

The chamber 6 is preferably designed in an at least essentially rigid manner. However, in principle, the chamber 6 can also be designed to be flexible and/or telescoping, in particular to be able to minimize the space requirement when not in use and/or for transport. In the illustrated embodiment, the chamber 6 is formed from a dimensionally stable, flexible material, and in terms of fluid engineering, the chamber 6 turns seamlessly into the dispensing device 7 in order to ensure a continuous path of flow. It is not ruled out, however, that the dispensing device 7 is connected to the chamber 6 in a resting and/or clamping manner and/or with a bayonet closure, with screw threading, or the like. Here also, however, other design solutions are possible.

The dispensing device 7 preferably has a soft end piece or forms the latter.

The dispensing device 7 is preferably designed as a nose adapter for insertion into the nostril 9 of the horse 5 or another animal, in particular a large animal, as indicated in a diagrammatic, cutaway view in FIG. 1. In particular, the inhaler 1 or the chamber 6 or the dispensing device 7 is thus designed in such a way that the aerosol 3 can be introduced into preferably the left nostril 9 of the horse 5. The chamber 6 and/or the dispensing device 7 can be transparent or formed from transparent plastic. In this way, the forming of aerosol 3 can be controlled.

Here, the dispensing device 7 preferably comprises an outlet 10, which engages or can be inserted into the nostril 9 or a nasal passage 11 of a horse 5 or another bodily orifice, and the chamber 6 or the dispensing device 7 can connect in a fluidic manner to the bodily orifice. The dispensing device 7 is especially preferably designed in such a way that the outlet 10 always ends in the correct nasal passage 11 and not in a blind passage. The dispensing device 7 can be at least essentially designed as described in International Patent Application Publication WO 94/17753 A1 and corresponding U.S. Pat. No. 5,666,948.

The user or patient, in particular a horse 5, can inhale the aerosol 3, whereby preferably air can be sucked in through the chamber 6.

The chamber 6 preferably comprises a volume of more than 0.05 l, in particular more than 0.1 l, and especially preferably approximately 0.1 to 0.4 l. Preferably, the size of the chamber 6 is matched or adapted to the inhaler 1 in such a way that the aerosol 3 that is generated when actuating the inhaler 1 can be taken up at least essentially completely from the chamber 6, in particular without the aerosol 3 or the sprayed pharmaceutical agent preparation 4 being significantly precipitated or deposited on the inside wall of the chamber.

Figure 2:
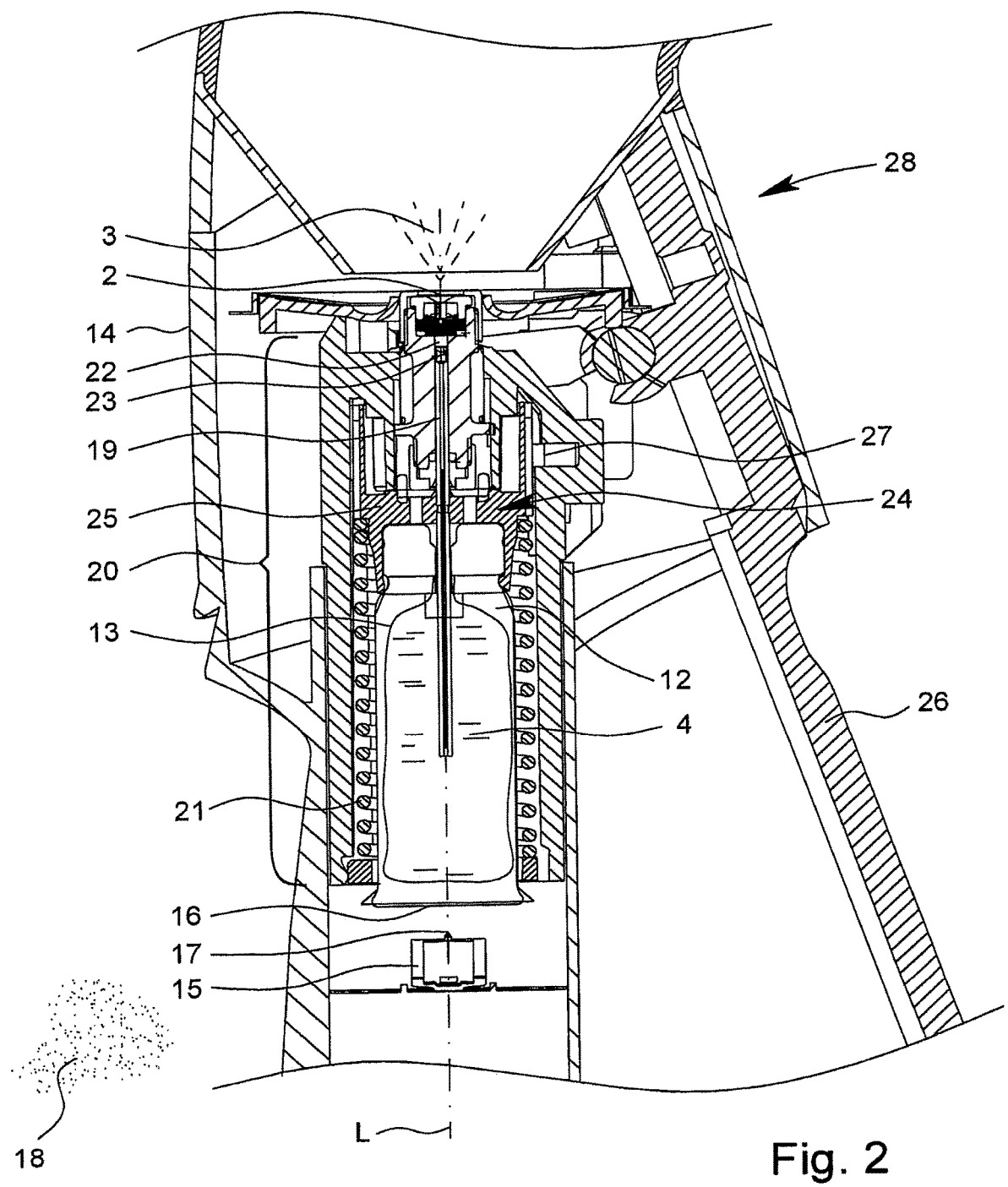
FIG. 2 is a sectional view of the inhaler in the area of the pressure generator in an untensioned state.
Figure 3:
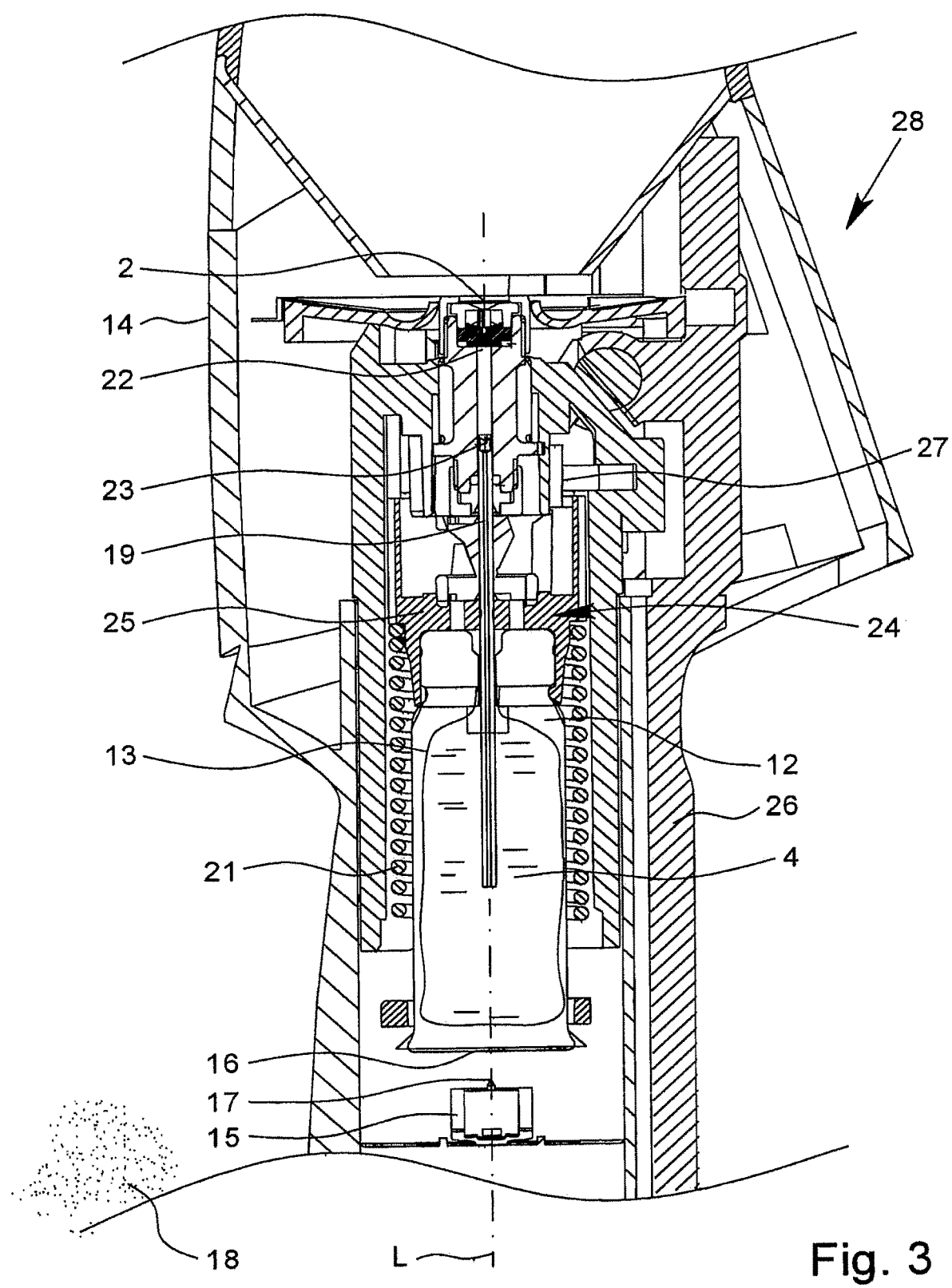
FIG. 3 is a sectional view of the inhaler in the area of the pressure generator in a tensioned state.

In FIGS. 2 and 3, a cutaway of the inhaler 1, according to the invention, is shown in the untensioned and the tensioned states.

The inhaler 1 is designed in particular as a Soft Mist Inhaler in the above-mentioned sense. The latter is explained in more detail below based on the cutaways according to FIGS. 2 and 3.

The inhaler 1 preferably comprises a container 12 with the pharmaceutical agent preparation 4. The container 12 thus forms a reservoir for the pharmaceutical agent preparation 4 that is to be sprayed. The container 12 preferably contains an adequate amount of pharmaceutical agent preparation 4 or active ingredient for multiple doses of the pharmaceutical agent preparation 4, i.e., to make possible multiple sprayings or applications. As disclosed in International Patent Application Publication WO 96/06011 A1 and corresponding U.S. Pat. No. 5,833,088, a typical container 12 occupies a volume of approximately 2 to 10 ml. It is preferred that the container 12 have a volume that is smaller than 50 ml, preferably smaller than 30 ml, and in particular smaller than 20 ml. In this way, a compact design of the inhaler 1 and consumability within the shelf life of the pharmaceutical agent preparation 4 can be ensured. With respect to the preferred design of the container 12, reference can be made in addition to International Patent Application Publication WO 00/49988 A2 and corresponding U.S. Pat. No. 6,988,496.

The container 12 is preferably designed essentially cylindrical or like a cartridge, and preferably, is securely integrated in the inhaler 1, in particular so that removal or replacement of the container 12 is impossible or at least is not possible without destroying or damaging it. It is thus preferred that the inhaler 1 is a disposable or throw-away product. However, other configurations are also possible.

The container 12 is preferably designed in a rigid manner, in particular whereby the pharmaceutical agent preparation 4 is taken up in a collapsible bag 13 in the container 12.

The inhaler 1 can preferably have a device for the forcing aeration of the container 12. In particular, in the case of initial tensioning, base-side tapping or opening of the container 12 is done. In particular, a spring 15 with axial action arranged in a housing 14 of the inhaler 1 comes to rest on the container base 16, which with a tapping element 17 taps the container 12 or a base-side, in particular gas-tight, seal the first time it is put in place for aeration.

Here, the device for the forced aeration is thus formed by the tapping element 17, which is held or formed by the spring 15. The tapping element 17 can also be realized without the spring 15. However, other design solutions are also possible.

It is noted that only the outside shell of the container 12 is opened in the tapping or in the aeration. The bag 13 remains preferably undamaged during the forced aeration. In the discharge of the pharmaceutical agent preparation 4 from the bag 13, the bag 13 can collapse, and for pressure equalization, ambient air 18 can flow back into the container 12 via the aeration or tapping opening.

Before the inhaler 1 is used for the first time, a preferably repeated tensioning and triggering of the inhaler 1 is performed. By this so-called priming, any air present is displaced from the pharmaceutical agent preparation 4 into a delivery tube 19 and into a pressure generator 20 and then into the discharge nozzle 2. Then, the inhaler 1 is ready for inhalation.

The amount of pharmaceutical agent preparation 4 delivered per stroke or per spraying process is preferably approximately 10 μl to 50 μl, in particular approximately 10 μl to 20 μl, and quite preferably approximately 15 μl.

A tensioning device 21, preferably a mainspring, is preferably integrated pre-tensioned in order to achieve a high delivery pressure. In the inhaler 1 according to the invention, the pressurization and delivery of the pharmaceutical agent preparation 4 during the spraying process are preferably produced only by energy stored in the tensioning device 21, in particular spring force. The inhaler 1 is thus preferably designed in that forming of an aerosol is independent of a tensioning process, even if prior tensioning can be a requirement for the forming of aerosol 3. Preferably, the inhaler 1 is designed in such a way that forming of aerosol—in particular the dose, the discharge rate and/or the discharge speed—is not affected independently of the tensioning process or by the tensioning process. In this way, a reliable metering can be achieved.

The inhaler 1 is preferably designed in such a way that the pharmaceutical agent preparation 4 in the pressure generator 20 in a pressure chamber 22 reaches a pressure of 5 MPa to 60 MPa, in particular 10 MPa to 50 MPa, in the dispensing. In the dispensing or spraying of the pharmaceutical agent preparation 4, a pressure of approximately 50 MPa to 60 MPa, in particular approximately 10 MPa to 30 MPa, is especially preferably reached at the discharge nozzle 2 or its nozzle openings. The pharmaceutical agent preparation 4 is then converted into the aerosol 3, whose droplets have an aerodynamic diameter of up to 20 μm, preferably approximately 3 μm to 10 μm. The spraying action or the spraying effect is realized or further supported by preferably intersecting streams, which are dispensed by the discharge nozzle 2.

The inhaler 1 is preferably designed in such a way that the aerosol 3 is dispensed at low speed, in particular at a speed of less than 2 m/s, especially approximately 1.6 m/s or less (in each case measured at a 10-cm interval from the discharge nozzle 2). The inhaler 1 is thus preferably designed as an SMI. The low dispensing speed can be realized or supported in particular by intersecting jets of the pharmaceutical agent preparation 4, which are dispensed into the discharge nozzle 2, and/or corresponding selection of the spring force of the tensioning device 21.

The inhaler 1 is especially preferably designed in such a way that the production of aerosol in each case lasts over 0.7 s, preferably essentially 1 s or longer, in particular over 1.5 s. The time period for spraying a dose or in the case of an actuation of the inhaler 1 is thus preferably over 0.75 s, in particular approximately 1 s or more.

The inhaler 1 also has a delivery device or a pressure generator 20 for conveying and spraying the pharmaceutical agent preparation 4, in particular in each case in a predetermined, optionally adjustable metered amount or for metered or meterable spraying. The inhaler 1 can thus administer the pharmaceutical agent preparation 4 in multiple defined doses, preferably as an aerosol 3. Preferably, in each case, a dose can be administered with an actuation of the inhaler 1.

The inhaler 1 or pressure generator 20 is designed in particular in such a way that the delivery, pressure generation and/or spraying is/are done without propellant, mechanically, and/or by the energy or force of an energy reservoir, in particular a spring loader, especially preferably by the spring force, in the illustrated embodiment by a mainspring, spiral spring or another tensioning device 21. However, other design solutions are also possible. In this case, it is preferred that the spraying be done independently of a manual operation, in particular independently of the speed of an actuation of the inhaler 1 or driven exclusively by the energy stored in the tensioning device 21.

The inhaler 1 or pressure generator 20 comprises a pump device 24, preferably with a holder 25 for the container 12 and/or with a delivery element, preferably with the delivery tube 19 designed as a capillary and with an optional valve, in particular a non-return valve 23. The pump device 24 is thus preferably an assembly of the pressure generator 20, which has the delivery tube 19 and means for its movement.

The pressure generator 20 can also have the pressure chamber 22 and/or the discharge nozzle 2, in particular in a transition area to the chamber 6.

The pump device 24 can be movable or drivable, in particular by the tensioning device 21. It is preferred that the pump device 24 for discharging the pharmaceutical agent preparation 4 be drivable exclusively by the tensioning device 21.

The container 12 is attached in the inhaler 1 via the holder 25, in particular in a clamping or resting manner, so that the delivery tube 19 plunges into the container 12. In this case, the holder 25 can be designed in such a way that the container 12 can be attached permanently, preferably in a resting manner.

The inhaler 1 comprises an actuating lever 26 for preferably axial tensioning of the tensioning device 21. When the tensioning device 21 is tensioned, the pump device 24 is preferably moved with the container 12, downward in the illustrated embodiment, and the pharmaceutical agent preparation 4—more precisely, the next dose—is suctioned off from the container 12 into the pressure chamber 22 of the pressure generator 20 via the non-return valve 23.

During subsequent depressurization of the tensioning device 21, in particular after actuation of a triggering device 27, the pharmaceutical agent preparation 4 is tensioned in the pressure chamber 22. To this end, the pump device 24 or the delivery tube 19 can be moved upward again in the case of the now-closed non-return valve 23 by depressurization of the tensioning device 21 and can now act as a plunger. Preferably, to this end, the pump device 24 is shifted linearly or axially with the delivery tube 19, in particular only by the tensioning device 21. This pressure expels the pharmaceutical agent preparation 4 through the discharge nozzle 2, whereby it is formed into the preferably respirable aerosol 3, as indicated in FIGS. 1 and 2.

FIGS. 4 and 5 show sections of the inhaler 1, according to the invention, with the tensioning mechanism 28 for tensioning the tensioning device 21, whereby the actuating lever 26 is shown in FIG. 4 in its rest position and in FIG.

5 in the tensioned position. In the tensioned position of the actuating lever 26, the tensioning device 21 is tensioned; in the rest position the tensioning device 21 is untensioned, i.e., relaxed, or only pre-tensioned.

In the variant embodiment shown, the inhaler 1 is designed so that it can be tensioned and/or triggered with one hand. This section is offset parallel to the longitudinal axis in order to show elements of the tensioning mechanism 28 that are arranged laterally to the discharge nozzle 2 and the pump device 24.

According to an aspect of this invention that can also be achieved independently, the tensioning mechanism 28 has a lever gear 29 for tensioning the tensioning device 21.

The pump device 24 and/or holder 25 is/are preferably axially movable by the lever gear 29. To this end, the pump device 24 and/or holder 25 can be guided axially, in particular by a cam or arm that is guided in a link. However, other solutions are also possible.

Furthermore, it is preferred that the pump device 24 and/or holder 25 be mounted in a manner that is stationary or kept from rotating. In this way, the tensioning mechanism 28 advantageously can be separated temporarily from the pump device 24 and/or holder 25 and coupled again.

The tensioning device 21 is designed to convey the pharmaceutical agent preparation 4 from the discharge nozzle 2 in a movement of the pump device 24 that is caused by the tensioning device 21. To this end, the pressure generator 20 can pressurize and/or spray the pharmaceutical agent preparation 4 by energy stored in the tensioning device 21.

Below, the lever gear 29 is first described functionally based on the lever arms and then described spatially based on the elements forming lever arms, since both the concept and the design also can be achieved independently and have advantageous aspects of this invention that can also be combined with one another since function and implementation complement one another.

The lever gear 29 especially preferably comprises an elbow lever 30. The elbow lever 30 has two lever arms 32, 33 that are connected to one another by a joint 31 (elbow) and that are also mounted in a hinged manner on the ends facing away from the common joint 31. If a force F' acts on the joint 31 of the elbow lever 30 perpendicular to the connecting line 34 of its outer end point, forces F'' are realized on the ends in the direction of the connecting line, and said forces are all the greater the smaller the angle $\alpha$ between the connecting line and lever. In particular, the force ratio is $F''=F'/(2 \tan \alpha)$. With increasing extension, i.e., the smaller the angle $\alpha$, the greater the gear reduction and thus the lever action of the elbow lever 30 are.

Preferably, the lever arms 32, 33 are at least essentially equally long, in particular more than 20 mm or 25 mm and/or less than 35 mm or 30 mm.

Furthermore, it is preferred that the lever gear 29 have at least two levers designed for gear reduction, preferably with an elbow lever 30 and a one-sided lever 35. The elbow lever 30 can be driven by means of the one-sided lever 35.

The one-sided lever 35 can be hinged on one end and can be loaded with a force F on another end. The one-sided lever 35 can have a shorter lever arm 36 with a lenght r1 and a longer lever arm 37 with a length r2, whereby the shorter lever arm 36 can correspond to the first lever arm 32 of the elbow lever 30. The force ratio under the assumption of perpendicular forces with force F acting on the end point of the second lever arm 33, facing away from the pivot point, for example by manual actuation, is $F'=F*r2/r1$. The length of the longer lever arm 37 preferably corresponds to more than twice, in particular more than three times, the length of the shorter lever arm 36.

Even if the indicated formulas because of the assumption of perpendicular forces only represent approximations and force parallelograms could be used to ensure more precise treatment, it is clear from the basic treatment that the levers 30, 35 in each case produce a gear reduction or force multiplication; the lever gear 29 is thus designed in multiple stages, in particular reduced in multiple stages. The lever gear 29, however, can also be designed in multiple stages in another way, in particular reduced in multiple stages.

The lever gear 29 offers the advantage that the lever action or gear reduction increases in the course of the tensioning process, in particular at the end of the tensioning process. In this way, it can be achieved that in the case of a manual actuation, the tensioning process is reliably performed until the end. Thus, a reliable metering can be achieved.

The lever gear 29 preferably comprises the actuating lever 26 and an arm 38, which can form the elbow lever 30 and/or the additional, preferably one-sided lever 35.

The actuating lever 26 can be hinged with a first end 39 at a housing 14 of the inhaler 1. The housing 14 can be designed in multiple parts. In this way, it can be provided that the actuating lever 26 is hinged on a housing part, which has at least one receptacle for the pump device 24 or the pressure generator 20 and/or whereby the housing part is designed with the actuating lever 26 to be taken up in a housing part of the housing 14 that forms a gripping area or handle. Preferably, the housing parts can be connected to one another in a resting manner and/or can be inserted into one another. The actuating lever 26 is especially preferably hinged at least on a housing part that holds the tensioning device 21, and it houses and/or forms a stop for the tensioning device 21. In this way, it can be ensured that forces generated by means of the actuating lever 26 can be introduced into the tensioning device 21. Other solutions are also possible, however, for example whereby the housing 14 can also be formed in one piece, in particular in one piece with the chamber 6 and/or with the dispensing device 7.

The actuating lever 26 preferably comprises an actuating section 40, in particular a gripping area, on an area facing away from the first end 39 or a pivot point 41 with the housing 14 or is designed in another way for manual actuation.

The actuating lever 26 can have a pressure position and a rest position. Preferably, the actuating lever 26 can pivot between the pressure position and the rest position.

In the pressure position, the actuating lever 26 can be brought up to the housing 14 of the inhaler 1, can rest against the housing 14 and/or be oriented at least essentially parallel to the housing section 38 adjacent to the actuating lever 26. The housing section 42 can form a handle or a grip. In the rest position, the actuating lever 26 preferably projects from the housing 14 or housing section 42. In this case, it can be provided that the actuating lever 26 at its pivot point 41 has a preferably hinge-like joint and/or rests against the housing 14, at an increasing distance from the pivot point 41, but arranged further removed from the housing 14, i.e., is swung away from the housing 14.

In the illustrated example, the actuating lever 26 can be pivoted around the pivot point 41, preferably by at least 10°, in particular at least 15°, and/or less than 25°, in particular less than 21°. However, other design solutions are also possible.

The actuating lever 26 can be arranged with the first end 39 in the housing 14, can be aligned to the housing 14, or can be mounted to pivot in the housing 14, in particular housing section 42. In this case, the housing section 42 can form a stop 43 for the actuating lever 26. The stop 43 preferably limits the pivoting angle of the actuating lever 26, in particular to make possible the above-mentioned pivoting areas.

By the arrangement of the actuating lever 26 with the first end 39 in the housing section 42, sections of the actuating lever 26 and the housing 14 that are movable against one another in a shearing way can advantageously be avoided, ensuring that the danger of injury by pinching can be reduced.

The aim 38 of the lever gear 29 is preferably hinged on the actuating lever 26. The arm 38 can be designed to connect the actuating lever 26 to the pump device 24. To this end, the arm 38 can be hinged on the actuating lever 26 on one side at a pivot point 44, which preferably corresponds to the joint 31 that is especially hinge-like, and on a second end that faces away from the pivot point 44, the arm 38 can be designed to introduce force into the tensioning device 21, ensuring that the tensioning device 21 can be tensioned. To this end, the arm 38 can be mounted to rotate on the pump device 24, the holder 19, or the tensioning device 21. However, alternative solutions are also conceivable, in which the tensioning device 21 can be tensioned via a lever gear 29.

The actuating lever 26 together with the arm 38 preferably forms the elbow lever 30. The latter is securely hinged preferably only on one end in the pivot point 41. The elbow lever 30 is driven or actuated in such a way that the pivot point 41 of the actuating lever 26 is shifted with the arm 38, ensuring that the pump device 24 preferably can move axially. To this end, the pump device 24 is preferably mounted axially. Furthermore, it is preferred that the pump device 24 be secured against rotating around the longitudinal axis L.

By the lever characteristic of the elbow lever 30, it is achieved that in the movement of the actuating lever 26 in the direction of the tensioned position, the force that is to be applied is reduced. As a result, the effect of this is that an actuation of the tensioning mechanism 28 during the course of the tensioning process at least in an area before the completion of the tensioning process requires a smaller force on the actuating lever 26. In the last section, this conveys the sensation that the actuating lever 26 almost moves by itself, because previously, greater force was necessary. Advantageously, the effect of this is that the actuating lever 26 is always swung into the pressure position.

The elbow lever 30 preferably forms a pressure point. The pressure point is characterized by a peak force in the pressurization plot or pressurization process. In the rest position, the elbow lever 30 is still comparatively far removed from the extension. The gear reduction is thus comparatively small. In a first section of the tensioning process, starting from the rest position of the actuating lever 26, the gear reduction by the elbow lever 30 is less greatly reduced than the increase in force by the increasing tensioning of the tensioning device 21. Consequently, the force that is to be applied with the actuating lever 26 for the tensioning process increases in an area starting from the rest position. By the nonlinear development of the gear reduction of the elbow lever 30, the active tensioning force increasing by the tensioning device 21 is then overcompensated. In the tensioning process, a maximum of the force to be exerted on the actuating lever 26 for the tensioning process is therefore developed. After exceeding the maximum, the necessary force for further tensioning the tensioning device 21 is lower because of the increasing extension of the elbow lever 30. Alternatively or additionally, the pressure point can be realized using a guiding surface with variable gradient or a screw or worm drive with variable screw lead.

Because of the comparatively low force that must be exerted in the last section of the pivoting of the actuating lever 26 from the pressure position to the actuating lever 26, it can be ensured that the actuating lever 26 usually reaches the pressure position. In this way, a reproducible and unchanged metering can be achieved.

It is preferred that the arm 38 be hinged to the actuating lever 26 between the pivot point 41 and the actuating section 40. In this way, the additional one-sided lever 35 is realized. The use of an elbow lever 30, in which the actuating section 40 acts directly on the pivot point 44 of the actuating lever 26 with the arm 38, is also possible as an alternative, however. The elbow lever 30 can thus also be realized without the one-sided lever 35, and it can be used as a tensioning mechanism 28.

The arm 38 is preferably designed to be L-shaped and/or in the manner of a fork. In this way, the arm 38 can encompass the delivery tube 19. In this way, the force exerted by the lever gear 29 can be introduced uniformly, in particular via the pump device 24, into the tensioning device 21. In this connection, the L shape helps to minimize the movement space for the elbow lever 30. In particular, the arm 38 is formed forklike or as a tensioning fork, whereby two preferably L-shaped sections are connected by an arm, whereby the arm is a joint and/or the ends of the sections facing away from the arm are designed for introducing force into the tensioning device 21. In this way, the housing volume can be minimized. As an alternative or in addition, the arm 38 can have an arc shape or the like.

The arm 38 preferably comprises polycarbonate (PC), polyoxymethylene (POM) and/or polybutylene terephthalate (PBT) or is formed therefrom, preferably reinforced, in particular glass-fiber-reinforced. The fork shape of the arm 38 in connection with the high forces, which occur in the tensioning of the tensioning device 21, results in special requirements on the stability of the material being used. Here, the production at least of the arm 38 made of the above-mentioned materials has turned out to be especially advantageous, surprisingly enough.

The pump device 24 preferably comprises a receptacle 45, a stop or an opposing bearing for rotatable mounting of the arm 38. In this way, the force can be transferred from the lever gear 29 to the pump device 24.

Preferably, the tensioning mechanism 28 is thus designed to mount the arm 38 in a tensioning movement of the lever gear 29 on the pump device 24 in such a way that a force from the lever gear 29 can be introduced into the tensioning device 21. As an alternative or in addition, the arm 38 can be detachable in a movement of the actuating lever 26 in the direction of the rest position of the pump device 24. It can thus be provided that the tensioning mechanism 28 or the lever gear 29 can be detached completely from the pump device 24. This advantageously allows a movement of the pump device 24 for administering fluid only by means of the force by the tensioning device 21. In this way, a reproducible metering and formation of aerosol can be ensured. The receptacle 45 is preferably mounted in a manner that is stationary, in particular relative to the longitudinal axis L. In this way, it is ensured that a tensioning mechanism 28 that is triggered by the pump device 24 can be later taken up again by the receptacle 45.

The inhaler according to the invention preferably comprises the triggering device 27, which is designed—when the tensioning process is completed—to secure the tensioning device 21 and/or the pump device 24 preferably snugly against movement. Furthermore, the triggering device 27 can be designed, in particular in the case of manual actuation, to make possible, in particular to trigger, a movement of the pump device 24 caused by the tensioning device 21. The triggering device 27 is thus preferably designed to block the forming of aerosol and to release it in the activation.

The housing 14, in particular the housing section 42, in particular a gripping area of the housing 14, can have, carry and/or encase the pressure generator 20, the pump device 24, and/or the tensioning device 21.

The tensioning mechanism 28 is preferably designed for conversion of a rotational movement, in particular a pivoting movement, of the actuating lever 26 in a linear tensioning movement that is axial here. However, other design solutions are also possible.

A pivoting movement in terms of this invention is preferably a rotational movement or a movement rotating around a pivot axis, which is limited in the freedom of movement in such a way that no complete rotation is possible. In particular, a pivoting movement in terms of this invention is a rotational movement, which is limited in design, preferably to less than 180°, in particular less than 90°.

The tensioning mechanism 28 is designed for tensioning the tensioning device 21. To this end, the tensioning mechanism 28 can turn a tensioning movement, in particular a pivoting movement, into a linear or axial movement in order to move the pump device 24 or the holder 25 via such a movement and/or to compress—and in this way, to pressurize—the tensioning device 21.

To tensioning the tensioning device 21, the pump device 24 can thus be moved by means of the tensioning mechanism 28 preferably axially, in particular along the longitudinal axis L. To this end, the pump device 24 or the holder 25 can be guided axially. By the axial movement, a force can be exerted on the tensioning device 21 in order to store energy in the tensioning device 21 by compression.

At the end of the tensioning process, the triggering device 27 can preferably automatically and/or by friction and/or by overlapping block a movement of the pump device 24 induced by the tensioning device 21. By activation of the triggering device 27, in particular by movement against a movement ensuring that the triggering device 27 blocks the pump device 24 against movement, the movement of the pump device 24 can be released, and the pump device 24 can be moved or driven by means of the tensioning device 21. In this case, the aerosol 3 can be formed from the pharmaceutical agent preparation 4 as described above.

The triggering device 27 can optionally be secured with a triggering blocker 46 against the triggering of the releasing of aerosol. In particular, with completion of the tensioning process or with blocking by the triggering device 27, the triggering blocker 46 can automatically secure the triggering device 27 against triggering. It is preferred that the triggering blocker 46 automatically releases the triggering device 27 as soon as the actuating lever 26 has again reached its rest position. Then, the triggering device 27 can be actuated, for example manually, in particular by actuating an actuating element 56, in particular a button, or automatically.

The triggering device 27 can be activated or actuated automatically when reaching the tensioned position and/or when the actuating lever 26 again reaches its rest position. In particular, the triggering by the triggering device 27 comprises a release of the pump device 24, so that the pump device 24 can be moved by the tensioning device 21 and in this way the aerosol 3 can be realized.

In a preferred embodiment, the triggering device 27 has a triggering delay or other device that produces a delay on the part of the pump device 24 relative to the actuating lever 26 moving into the rest position. In this way, it can be ensured that even without an actuating element 56, triggering and releasing of aerosol is made possible in a reliable way and with a reproducible dose.

For example, a means is provided that makes possible a fully automatic triggering after the actuating lever 26 has left its tensioned position. In particular, the triggering is done after the actuating lever 26 has been swiveled away from its tensioned position or from a position that faces the housing 14 by at least 1°, preferably at least 2°, and in particular at least 3°. In this way, an automatic triggering can be achieved with a pressure generator 20 that makes the tensioning mechanism 28 lag or a pump device 24 that makes the tensioning mechanism 28 lag. In addition to the reliable metering, this offers the advantage that a triggering with a very small delay is made possible by a user disengaging the actuating lever 26. However, other solutions are also possible, for example a triggering without a delay. In this case, the actuating lever 26 is preferably moved back at sufficient speed into the rest position, so that the tensioning mechanism 28 does not affect the forming of aerosol, in particular whereby a movement of the pump device 24 makes the movement of the tensioning mechanism 28 lag. It is preferred that the pump device 24 can be moved for the forming of aerosol without contact with or under the influence of the tensioning device.

In one method, the inhaler 1 can be tensioned via the elbow lever 30, whereby the elbow lever 30 acts on the tensioning device 21 and preferably compresses the latter axially.

The actuating lever 26 can have a reset element 47 such as a spring, which is designed to move the actuating lever 26 into its rest position or to hold it there. In principle, the tensioning device 21 can bring the actuating lever 26 back into the rest position via the tensioning mechanism 28. It is preferred, however, that after the tensioning process, the tensioning mechanism 28 be completely detached from the pump device 24, so that the pump device 24 can be moved independently of the tensioning mechanism 28 by the tensioning device 21. Therefore, it is preferred that a reset element 47, independent of the tensioning device 21, be provided, for example a spring, a rubber seal, or the like, acting on the actuating lever 26 in the direction of the reset position.

A pivot axis of the actuating lever 26 at the pivot point 41 can be arranged crosswise and spatially offset relative to the longitudinal axis L of the inhaler, in particular an axis that corresponds to the direction of movement of the pump device 24 and/or the discharge direction of the discharge nozzle 2. In this way, it can be achieved that the pivot point 41 of the actuating lever 26 with the housing 14 does not impede the flow of the aerosol 3. Furthermore, in the spatially offset arrangement of the pivot point 41 relative to the longitudinal axis L, the elbow lever 30 can be operated closer to its extension, i.e., with a greater lever action.

According to another aspect of this invention that can also be achieved independently, the inhaler 1 is designed for metered spraying of the pharmaceutical agent preparation 4 and has an indicator 48, which has a metering ring 50, mounted to rotate around an axis of rotation 49, with indicator means 51 for displaying a number of still available or already administered doses, in particular, i.e., a dose indicator.

Figure 6:
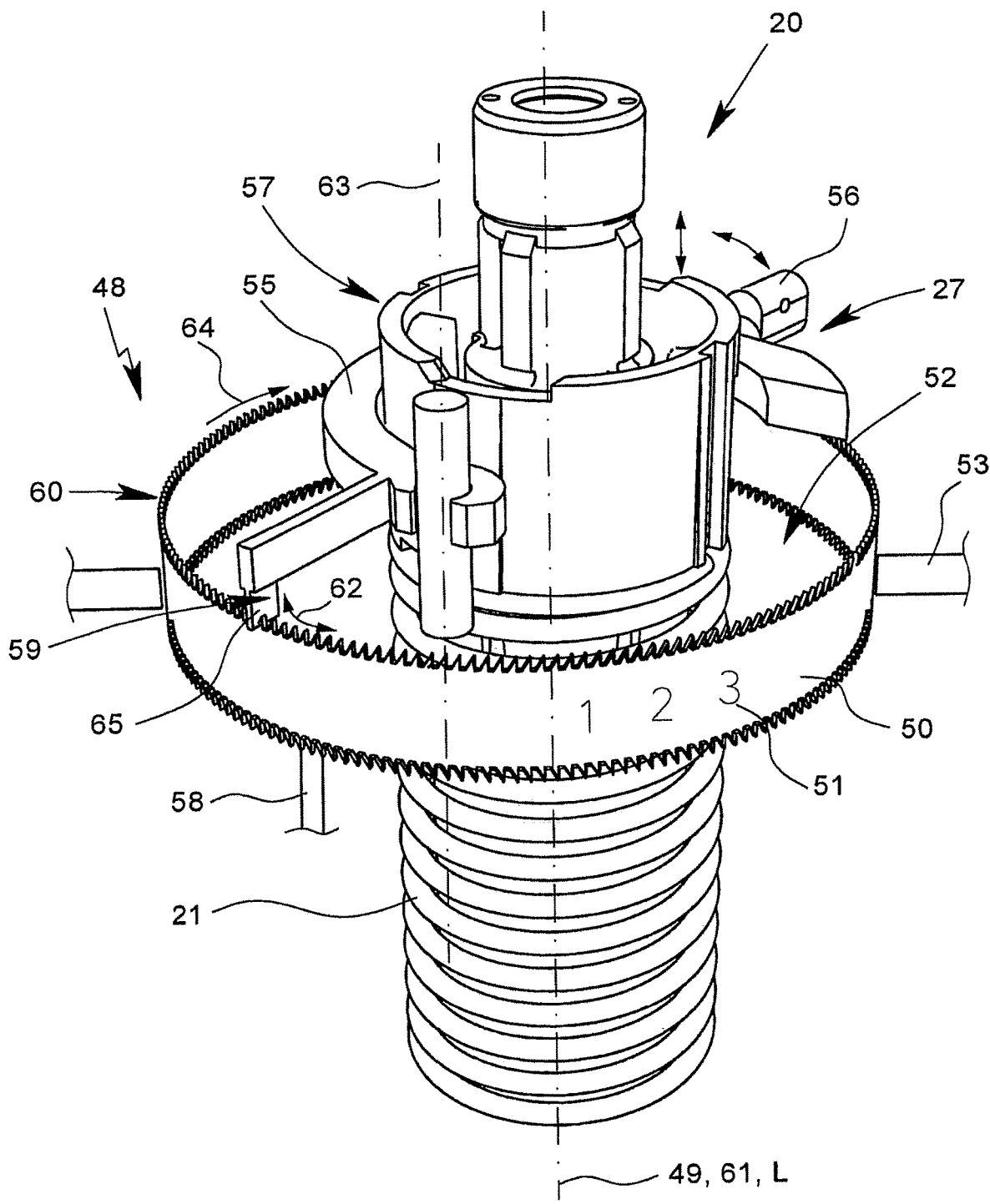
FIG. 6 is a simplified, perspective view of the inhaler in the area of the indicator for display of doses that are still available or already administered with a pump device and tensioning device.
Figure 7:
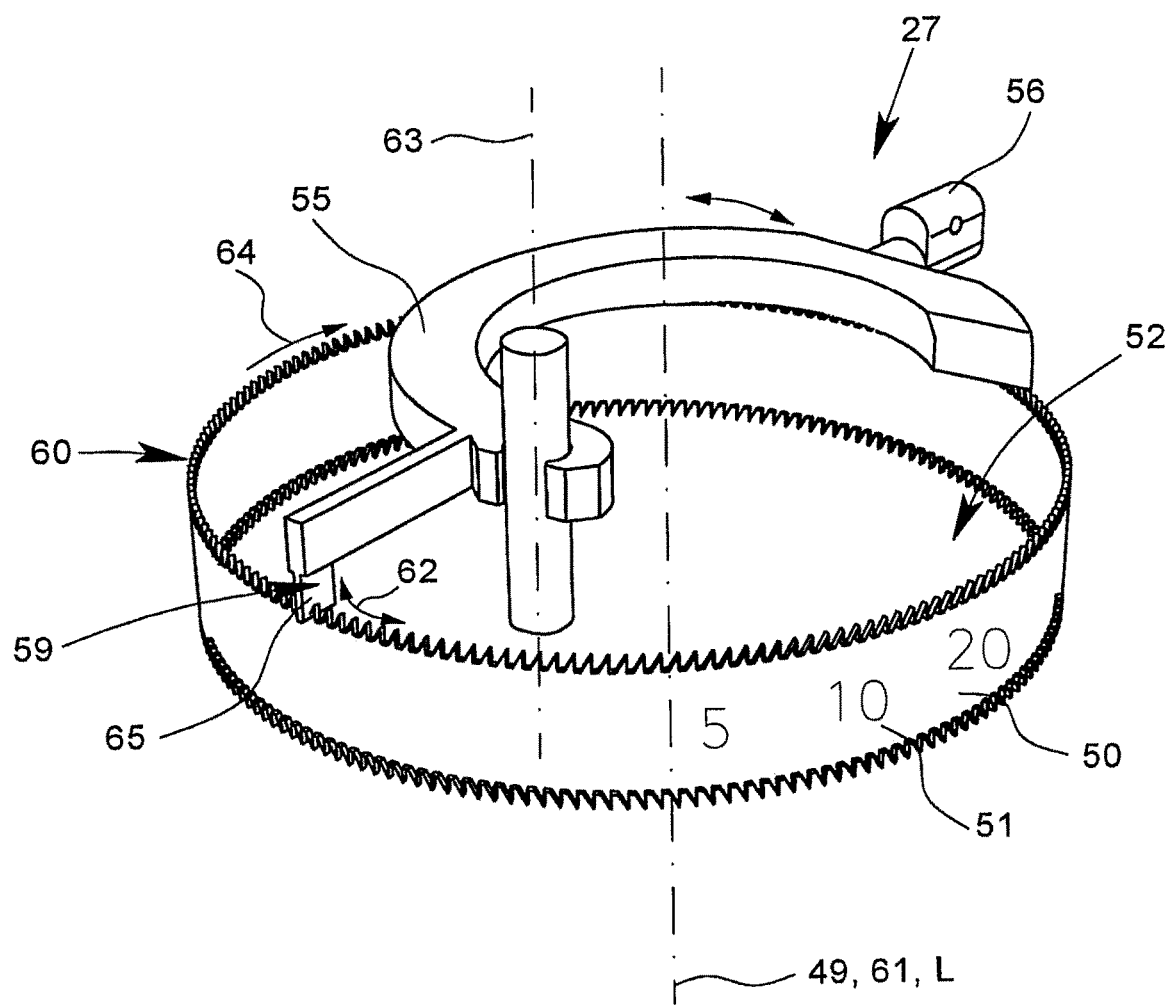
FIG. 7 is a simplified, perspective view of the inhaler in the area of the indicator for display of doses that are still available or already administered without the pump device.

In a perspective view, FIGS. 6 and 7 show essential parts of the indicator 48 with and without the pressure generator 20.

The metering ring 50 preferably comprises a preferably axial through passage 52. The through passage 52 can be arranged and designed in such a way that the pressure generator 20 or parts thereof, in particular the pump device 24, can be arranged in the through passage 52. The metering ring 50 can thus be arranged around the pressure generator 20 or the pump device 24.

The metering ring 50 can be guided in a groove or link. As an alternative or in addition, other guide means, in particular at least three, preferably at least four, guide arms 53 can be provided, which are mounted to rotate the metering ring 50 and/or to prevent a lateral or axial movement.

As indicator means 51, for example, the metering ring 50 can have imprinted dashes, numbers which identify the number of does that are still available or have already been administered. The indicator means 51 are preferably applied to a radial front side. As an alternative or in addition, the metering ring 50 can also have—as an indicator means 51—a color indicator, for example a marking or a marked area, which can correspond to a remaining volume of the pharmaceutical agent preparation 4, in particular to display an inventory. Different indicator means 51 can furthermore be combined; for example, the same metering ring 50 can include still available or already administered doses, dashes to display in each case a dose consisting of multiple triggerings and/or a colored, for example, red, marked area, which can warn of a reduced remaining amount of the pharmaceutical agent preparation 4. However, other solutions are also possible.

The inhaler 1, in particular the housing 14, can have a window 54 for visibility of the metering ring 50 arranged in the inhaler 1 (cf. also FIG. 1).

According to an aspect of this invention that can also be achieved independently, the metering ring 50 can be moved or rotated by the triggering device 27. The triggering device 27 can be assigned to the pressure generator 20, in particular whereby the triggering device 27 can block and/or release the pressure generator 20. The pressure generator 20 is especially preferably designed or works mechanically as a pump. The same triggering device 27 can be used for driving the metering ring 50.

According to another aspect of this invention that can also be achieved independently, the inhaler 1, in particular the triggering device 27, has a pivot arm 55, whereby the metering ring 50 can be moved or rotated by pivoting the pivot arm 55. In particular, the pivot arm 55 is designed as a blocking ring or section of a blocking ring for blocking and releasing the pressure generator 20.

It is preferred that, by means of the pivoting movement of the pivot arm 55, the metering ring 50 be driven in order to have the display track the number of still available or already dispensed doses in preferably each individual triggering of the inhaler 1. In particular, the spraying by the triggering device 27 or by pivoting the pivot arm 55 can be released, and the metering ring 50 can be driven simultaneously and/or with the same movement by the triggering device 27 and/or by pivoting the pivot arm 55.

In the illustrated embodiment, the triggering device 27 has an actuating element 56, in particular a snap fastener, for manual triggering of the forming of aerosol. The actuating element 56 can drive the pivot arm 55. In particular, the actuating element 56 is formed in one piece with the pivot arm 55 or in another way is coupled to the latter. However, other solutions are also possible.

The metering ring 50 can be transported with release of the pump device 24 or the tensioning device 21. Then, the tensioning device 21 is tensioned again with the tensioning mechanism 28. As an alternative or in addition, the metering ring 50 is driven in—or by—locking or pivoting of the pivot arm 55.

When the tensioning process is completed, the pivot arm 55 can form a positive fit with a positive device 57 of the pressure generator 20 or the pump device 24, ensuring that the pressure generator 20 or the pump device 24 is blocked against triggering or the forming of aerosol. In particular, it is provided that the pivot arm 55 overlaps a part of the pump device 24, in particular the holder 25, by pivoting and herewith prevents the movement of the pump. In particular, the holder 25 or an edge of the holder 25 therefore forms the positive device 57. However, other solutions are also possible.

The pivot arm 55 can be pre-tensioned against the positive device 57, preferably against the pump device 24, in particular against the holder 25, so that the pivot arm 55 can secure the pressure generator 20 automatically against triggering by friction when the tensioning process is completed. In the illustrated embodiment, the pivot arm 55 is clamped in particular by means of a spring against the pump device 24. At the end of the tensioning process, the pivot arm 55 reaches the coupling device 60, in particular an upper edge, recess, or the like, of the pump device 24, preferably automatically swings laterally over the edge, into the recess, or in another way forms a positive fit, which prevents an axial pump movement of the pump device 24.

By pivoting the pivot arm 55, in particular by locking the pump device 24, a drive of the metering ring 50 can be prepared, so that the metering ring 50 can be rotated (again) with triggering.

It is preferred that the actuating lever 26 be longer than 10 cm, preferably longer than 12 cm, in particular longer than 14 cm and/or shorter than 20 cm, preferably shorter than 18 cm, and in particular shorter than 16 cm, and/or can be swiveled by more than 5°, preferably more than 10°, in particular more than 15° and/or less than 45°, preferably less than 40°, and in particular less than 35°.

Relative to the pivoting movement of the pivot arm 55, reference is made to the definition given above.

The inhaler 1 preferably comprises a non-return device 58, which blocks a rotation of the metering ring 50 in one direction and/or allows a rotation of the metering ring 50 only in a direction of rotation.

To drive the metering ring 50, the triggering device 27, in particular the pivot arm 55, has a drive device 59, which is designed to rotate the metering ring 50, preferably by pivoting the pivot arm 55.

The metering ring 50 can have a coupling device 60 for driving the metering ring 50 by the drive device 59, in particular a drive track or a positive device, preferably a gear. In the illustrated embodiment, the coupling device 60 is formed on a front surface and/or by a gear, in particular with asymmetrical tooth flanks. The drive device 59 can be designed to engage in the coupling device 60 of the metering ring 50.

Preferably, the drive device 59 comprises a carrier, a detent pawl, a tongue, or the like or is designed as a carrier, detent pawl or tongue. In particular, the drive device 59 is flexible, bendable, and/or has an edge for engagement in the coupling device 60 or gear for driving the metering ring 50. In this case, it can be provided that the drive device 59 engages in the gear in the movement of the pivot arm 55 in the tensioning direction or in releasing or triggering direction, and in this way drives the metering ring 50.

The pivot arm 55 can pivot preferably more than 2°, in particular more than 4°, and/or less than 45°, preferably less than 30°, in particular less than 20°, and in the illustrated embodiment approximately 5° to 10°.

During a tensioning process, in particular when the pivot arm 55 is swung in order to block the pressure generator 20 or during a triggering process when the pivot arm 55 is swiveled in order to release the pressure generator 20, the drive device 59 can engage with the coupling device 60 and can be moved via or relative to the coupling device 60. In this way, the drive device 59 can be moved into a position in which the drive device 59 can be coupled at another point in the coupling device 60, in particular in the next or another tooth of the gear. Thus, the metering ring 50 can be rotated successively, preferably triggering for triggering, in each case by at least essentially the same angle. It is preferred that the drive device 59 and the coupling device 60 be designed and arranged relative to one another so that the drive device 59 drives the coupling device 60 in one direction and can be shifted in the opposite direction relative to the coupling device 60.

The coupling device 60 is preferably provided on a front side of the metering ring 50, and the indicator means 51 is provided on an outer peripheral surface of the metering ring 50.

It is preferred that the angle of rotation of the metering ring 50 be between 0.5° and 1.5° per triggering. In this way, on the one hand, a precise enough display can be achieved, and, on the other hand, a sufficient number of doses that can be metered can be achieved. Preferably, the metering ring 50 is designed to indicate more than 120, preferably more than 150, and/or less than 250, preferably less than 220, and in particular approximately 180 doses.

A characteristic of this solution is that the drive device 59 can be moved preferably by pivoting the pivot arm 55 around a first axis of rotation 61 on a driving means track 62. Furthermore, the coupling device 60 of the metering ring 50 can be moved around a second axis of rotation 63 on a metering ring track 64. It is especially preferred that the driving means track 62 and the metering ring track 64, indicated in FIGS. 6 and 7 by arrows, be different. In particular, the driving means track 62 and the metering ring track 64 intersect, preferably only once. Also, the position of the axes of rotation 61, 63 can be different. In particular, the first axis of rotation 61 of the driving means 62 lies within the metering ring track 64 or the metering ring 50. Furthermore, the driving means track 62 and the metering ring track 64 can have different radii. It is preferred that the first axis of rotation 61 and the second axis of rotation 63 be arranged at least essentially parallel to one another or point spatially in the same direction.

The drive device 59 can preferably be rigidly connected and/or formed integrally with the blocker ring 55 via an arm.

The drive device 59 and the corresponding coupling device 60 are preferably formed by a gearwheel and detent pawl. As an alternative or in addition, however, this can also be a friction means and/or a friction track, whereby the drive device 59 forms a frictional connection with the coupling device 60 for driving the metering ring 50. In this case, the non-return device 58 can also prevent a back-and-forth movement of the metering ring 50. In this way, a continuous metering movement of the metering ring 50 can thus be ensured. However, other solutions are also possible.

The drive device 59, however, especially preferably comprises a detent pawl or another carrier, and the coupling device 60 comprises an especially asymmetrical gear. In this connection, it is preferred that the drive device 59 have a guide surface 65, which is designed to rotate the metering ring 50 by moving the guide surface 65 along the coupling device 60, in particular the gear, of the metering ring 50. In this way, a pivoting of the pivot arm 55 can be implemented especially effectively in a rotational movement of the metering ring 50.

The guide surface 65 can be inclined relative to a tangent to the driving means track 62, preferably so that the movement of the guide surface 65 makes possible an advancing of the metering ring 50. In particular, the guide surface 65 moves the metering ring 50 by means of a tooth of the coupling device 60 with a movement of the drive device 59 with the guide surface 65, which removes the drive device 59 from the second axis of rotation 63 of the metering ring 50. However, other design solutions are also possible.

The drive device 59 can be pre-tensioned against the coupling device 60. With this, it can be achieved that the drive device 59 can slide over the coupling device 60 when moving in a direction blocked by the non-return device 58 and can drive the metering ring 50 again to a changed position. To this end, the drive device 59 can be spring-loaded or elastically deformable. Furthermore, it is preferred that the drive device 59 be tongue-shaped, elongated and/or flat. In this way, a pre-tensioning can be realized especially easily and effectively, which ensures a secure drive and at the same time supplies the elasticity that prompts the drive device 59 to move toward the rotational direction relative to the coupling device 60.

The drive device 59 is preferably fastened to the pivot arm 55, molded-on and/or formed in one piece with the pivot arm 55. However, other solutions are also possible. In particular, the drive device 59 can also be shifted only laterally in order to drive the metering ring 50. In this case, it is preferred in addition that the metering ring track 64 and the now straight drive means track 62 intersect. In particular, the guide surface 65 can be designed in such a way that guiding of the guide surface 65 along the coupling device 60 makes possible a drive of the metering ring 50. However, still other design solutions are also conceivable.

As a whole, this invention can make possible the drive of an indicator for displaying a number of still available or already administered doses, in particular the metering ring 50 by pivoting the pivot arm 55 and/or by triggering the pressure generator 20.

In a possible alternative, the pivot arm 55 is not provided for locking the pump device 24 and/or for triggering the forming of aerosol. The pivot arm 55 is thus not necessarily part of the triggering device 27, but rather it can also be used independently of the triggering device 27 for driving the indicator 48. Moreover, other indicators that are not necessarily operated with a metering ring 50 can also be driven by the pivot arm 55 according to the invention. In particular, the metering ring 50 can also be a metering ring 50 that is formed to be only partially annular. As an alternative or in addition, metering rods, metering gauges, in particular on an unwinding roller or the like, or other carriers can be used for the indicator means 51, which also are driven by means of the pivot arm 55. However, the depicted combination of metering ring 50 and drive device 59 is especially preferred.

The metering ring 50 can have an outside diameter that is larger than 1 cm, preferably larger than 1.5 cm, in particular larger than 1.8 cm, and/or smaller than 4 cm, preferably smaller than 3.5 cm, and in particular smaller than 3 cm. This makes possible a detailed application of the indicator means 51, in particular a fine scale.

The indicator means 51 preferably comprises lines, numbers, or the like. It is not necessary that the numbers immediately follow one another. For example, the indicator means 51 has numbers in intervals of five or ten. In an alternative, the indicator means 51 comprises a dose scale. For example, when using the inhaler 1 in larger animals, a repeated triggering may be necessary in order to reach the necessary total dose. In this connection, a dose scale can be used as an indicator means 51, whereby the dose scale in each case comprises breakdowns for a specific number of multiple triggerings. For example, the indicator means 51 can have markings for each fifth, sixth, seventh, eight, ninth or tenth triggering. Based on the application or patient, the inhaler 1 can then have an indicator means 51 that is set up accordingly.

Figure 8:
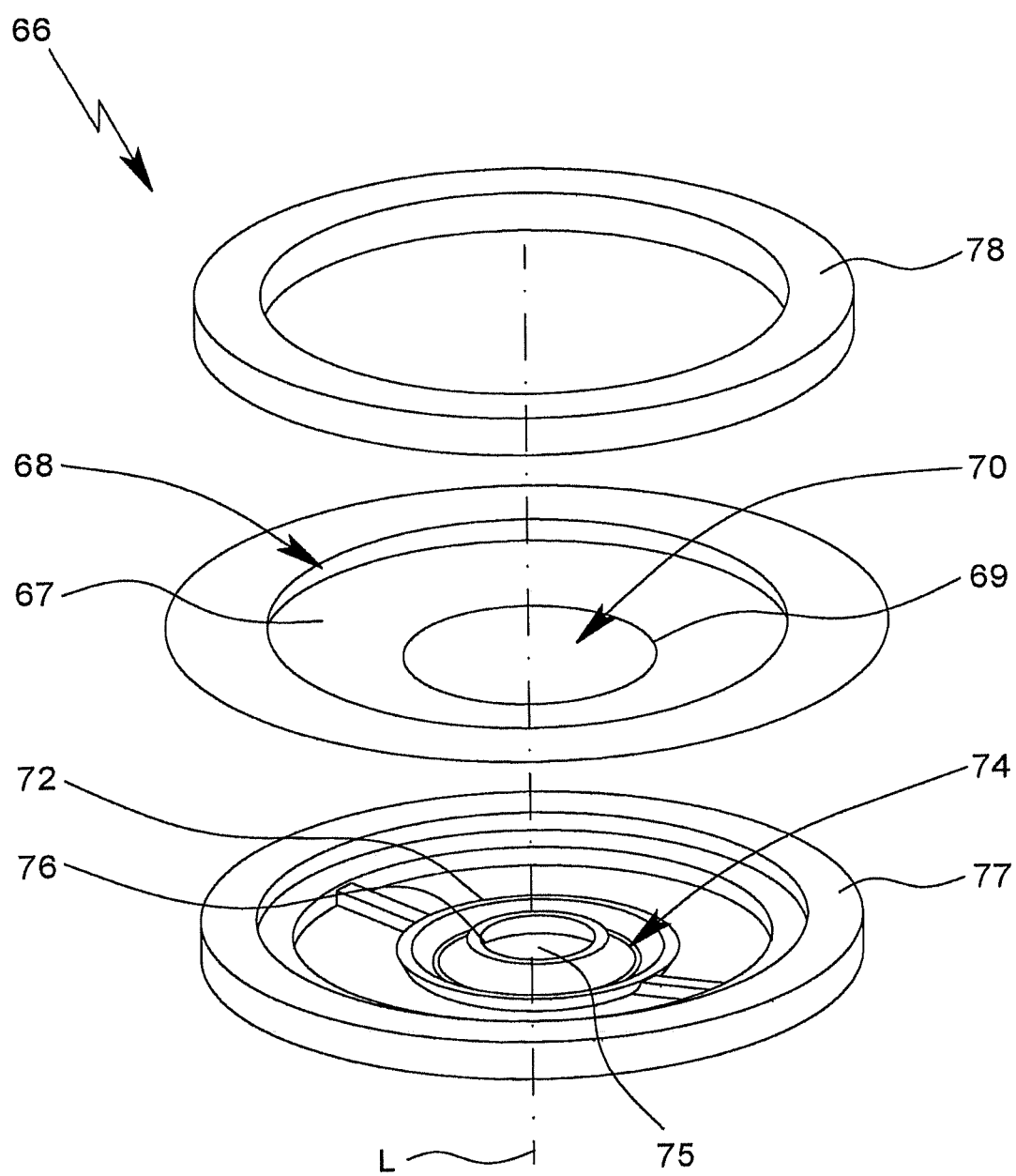
FIG. 8 is an exploded perspective view of an inhalation valve according to the invention.
Figure 9:
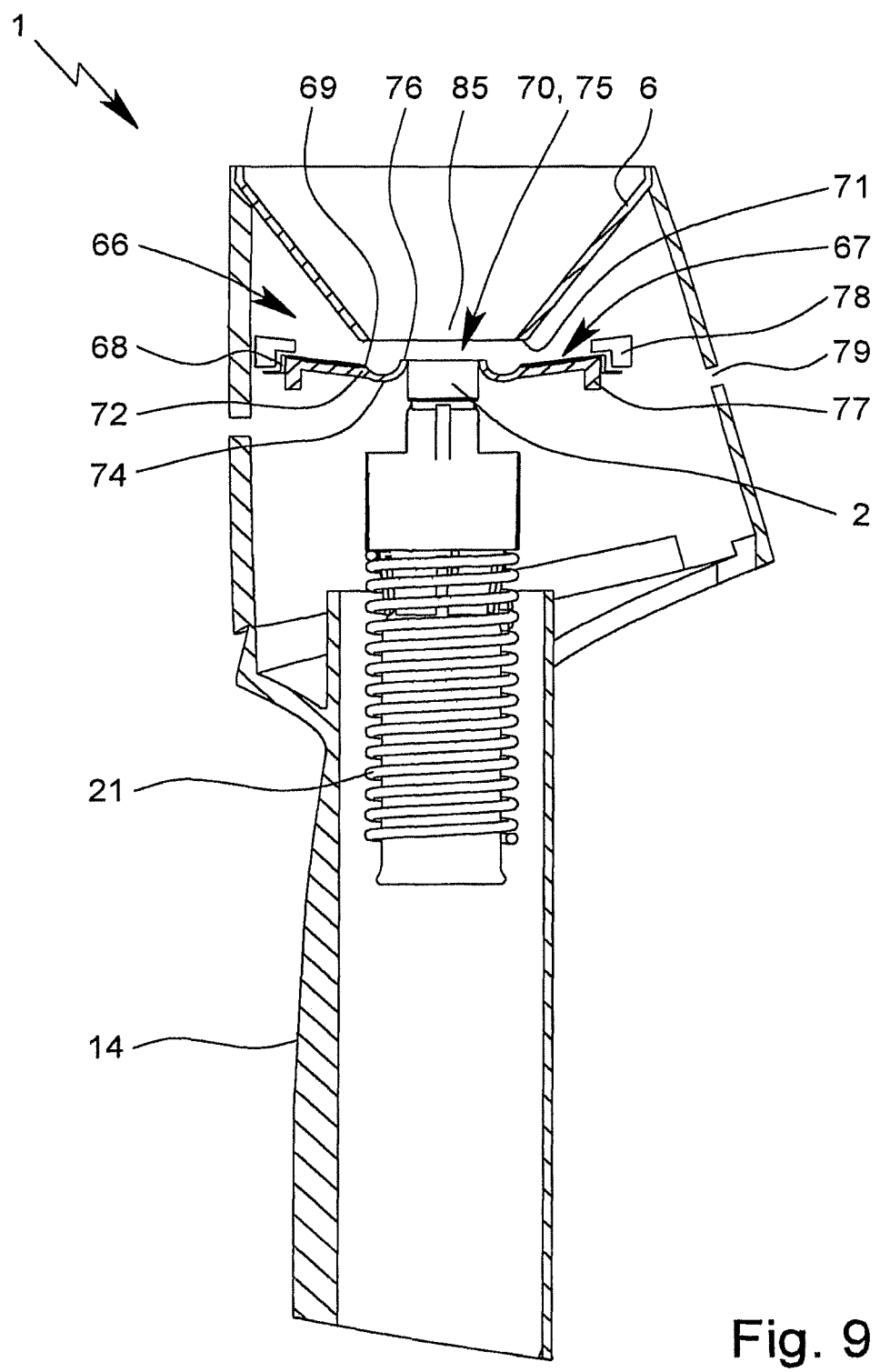
FIG. 9 is a simplified, partial sectional view of the inhaler in the area of the inhalation valve in a closed state.
Figure 10:
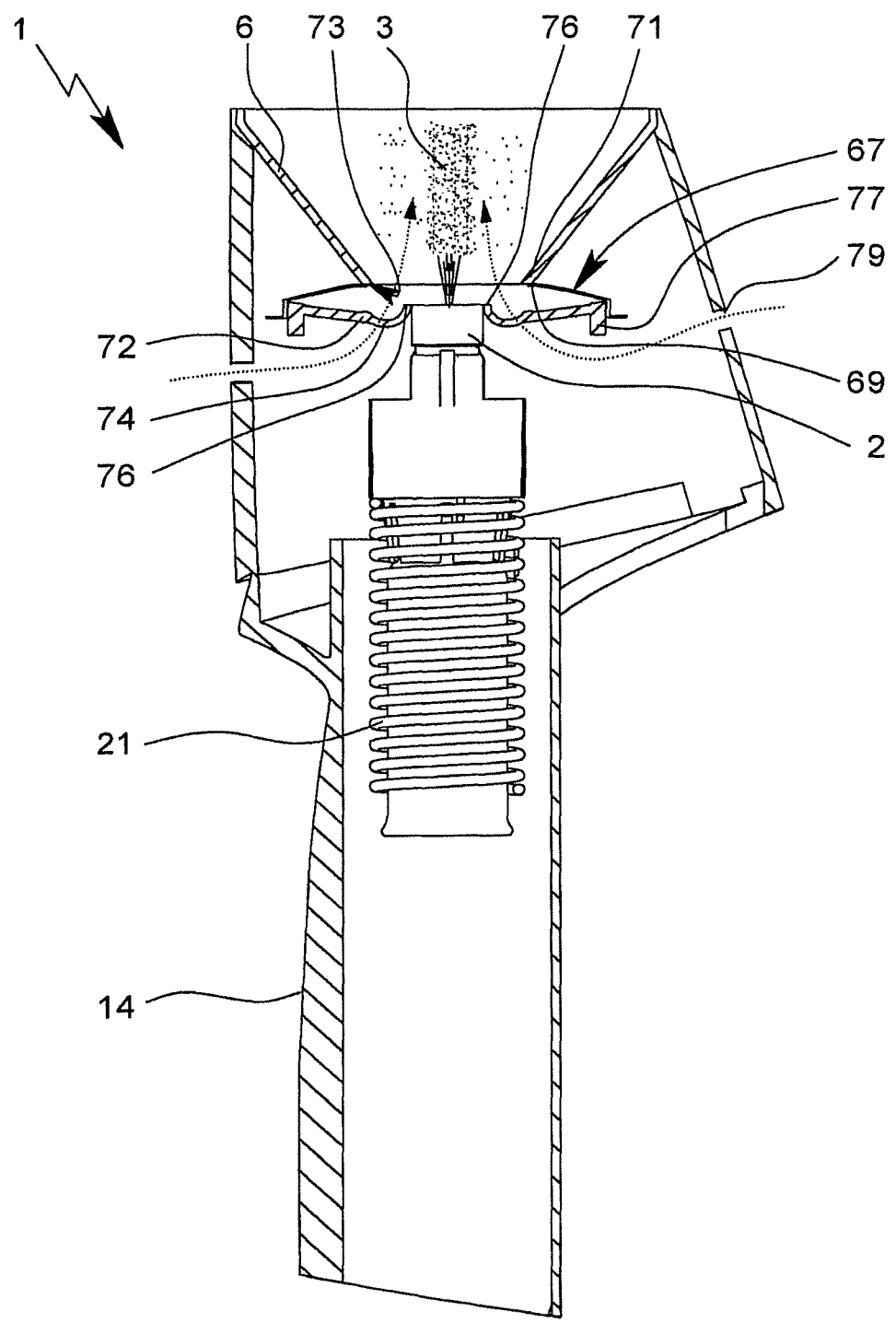
FIG. 10 is a simplified, partial sectional view of the inhaler in the area of the inhalation valve in an open state.

For the inhalation of the aerosol 3 by means of the inhaler 1, preferably an inhalation valve 66 is provided, which is depicted in FIG. 8 as an exploded drawing, closed in FIG. 9, and open in FIG. 10. The inhalation valve 66 comprises a valve element 67, in particular a valve flap or membrane. The valve element 67 is preferably flexible, bendable, flat, thin, disk-like, conical at least in sections and/or membrane-like. The valve element 67 can have silicone or LSR (liquid silicone) or be formed therefrom.

The inhalation valve 66 is preferably arranged outside of the chamber 6, but can also form part of the chamber 6.

The inhalation valve 66 is designed for intake of ambient air 18 into the chamber 6, whereby the inhalation valve 66 is preferably blocked or throttled in the reverse direction in particular so that in the case of exhalation, no air and no aerosol from the chamber 6 can be released through the inhalation valve 66 into the environment. In the illustrated embodiment, the inhalation valve 66 is preferably designed as a non-return valve or membrane-like valve, with or without pre-tensioning in the closed position. However, other design solutions are also possible.

According to an aspect of this invention that can also be achieved independently, the valve element 67 is designed to be annular and comprises an outer edge 68 and an inner edge 69. The valve element 67 is fastened to the outer edge 68, and the inner edge 69 forms the boundary of an through passage 70 of the valve element 67. Furthermore, the inhalation valve 66 has a valve body seat 72 for the valve element 67, which corresponds to the inner edge 69.

The inhalation valve 66 is preferably designed so that in the case of excess pressure in the chamber 6 relative to the environment or in the case of a respiratory process in the chamber 6, the inhalation valve 66 closes, whereby the valve element 67 rests or is pressed snugly on the valve body seat 72—cf. FIG. 10. In a respiratory process, the inhalation valve 66 is opened, and this allows ambient air 18 to flow in through the inhalation valve 66 into the chamber 6. To this end, it is provided that the valve element 67 forms an opening, which makes it possible, by deforming on its inner edge 69, for the ambient air 18 to flow in.

In the illustrated embodiment, the outer edge 68 of the valve element 67 is snugly fastened all the way around. An opening of the inhalation valve 66 is carried out on the inner edge 69 of the valve element 67. Here, the valve element 67 is lifted from the valve body seat 72 by a pressure differential in the flow direction, ensuring that an opening in the area of the through passage 70 is made. The inhalation valve 66 thus preferably opens only on the inner edge 69.

The discharge nozzle 2 is preferably arranged in the through passage 70. As an alternative or in addition, the discharge nozzle 2 can be arranged so that an aerosol 3 released by the discharge nozzle 2 can be released through the through passage 75 or can be introduced into the chamber 6.

The combination of the aerosol release in the area of the through passage 75 or 70 and the opening of the inhalation valve 66 on the inner edge 69 advantageously results in that an air stream that passes through the inhalation valve 66 can form a jacket around the aerosol 3, as is known from, for example, turbofan engines of aircraft for sound insulation. The concentration of active ingredients is thus preferably reduced in the edge area of the flow. In this way, it is achieved that only comparatively few particles of the pharmaceutical agent preparation 4 or the aerosol 3 come into contact with a wall of the chamber 6 or the dispensing device 7 and are deposited. The inhalation valve 66 according to the invention thus advantageously results in an especially efficient releasing of the aerosol 3 with the pharmaceutical agent preparation 4.

According to another aspect of this invention that can also be achieved independently, the inhaler 1 has a stop 71 for the valve element 67 on a side of the valve element 67 that faces away from the valve body seat 72. The stop 71 can prevent an overexpansion and damage of the valve element 67. As depicted by way of example in FIG. 10, the stop 71 furthermore makes it possible, when the valve element 67 is at rest, to pre-specify a flow geometry, which in an adequate valve opening is at least essentially independent of the size of the volume flow, which passes through the open inhalation valve 66.

According to another aspect of this invention that can also be achieved independently, the chamber 6 with the valve element 67 in the open position forms a closed flow wall 73 and/or nozzle. In particular, it is preferred that the chamber 6 have the stop 71 that corresponds to the inner edge 69 of the valve element 67, on which the valve element 67 rests snugly in the open position, ensuring that the closed flow wall 73 is realized. In this way, in an advantageous way, flow detachment, which would be associated with the forming of eddies, can be avoided, whereby eddies can cause particles of the pharmaceutical agent preparation 4 from the aerosol 3 to make increased contact with the chamber 6 or to precipitate in the chamber 6. In particular, it is preferred that the valve element 67 with the chamber 6 form a nozzle, in particular by a flow cross-section decreasing by means of the valve element 67 in the direction of flow and then increasing by the chamber 6 in the direction of flow. In this way, in particular a valve nozzle can be realized, ensuring that a forming of aerosol can be supported by the discharge nozzle 2.

The inhalation valve 66 is preferably rotationally symmetrical to the longitudinal axis L of the inhaler 1 or to a dispensing direction of the discharge nozzle 2. In this way, a passage of the air flow that is especially free of eddying is made possible by the inhalation valve 66, thereby reducing the probability that aerosol components will then condense.

According to another aspect of this invention that can also be achieved independently, the inhalation valve 66 has a collecting device 74 for solid and/or liquid substances. The collecting device 74 preferably has the valve body seat 72 and/or a receptacle 45 for the discharge nozzle 2. The collecting device 74 can have a through passage 75 to accommodate the discharge nozzle 2 or for the aerosol 3 being run through.

The collecting device 74 can be designed to collect secretions or condensates, in particular nasal discharges or respiratory condensates, in order to prevent the latter from crusting and blocking the inhalation valve 66, in particular the valve element 67, and/or the discharge nozzle 2 or an opening of the discharge nozzle 2.

The collecting device 74 can adjoin the valve body seat 72 or form the valve body seat 72. In the illustrated embodiment, the collecting device 74 is formed in the shape of a groove, bowl or shell. In particular, the collecting device 74 has an annular groove, whose outer edge forms the valve body seat 72 and/or whose inner edge has a sealing edge or sealing lip 76, which forms the through passage 75, an opening for accommodating and/or guiding the discharge nozzle 2 through. In one alternative, the valve body seat 72 can directly form the sealing edge or sealing lip 76 for accommodating and/or guiding the discharge nozzle 2 through, in particular when the inhaler is realized without a collecting device 74. Guiding the discharge nozzle 2 or the aerosol 3 through can also be implemented in other ways.

In general, it is preferred that the discharge nozzle 2 be taken up in the inhalation valve 66, be encompassed by the inhalation valve 66, and/or be arranged in the through passage 70 of the valve element 67. As an alternative or in addition, it is provided that the pharmaceutical agent preparation 4 or the aerosol 3 is guided through the through passage 70 into the chamber 6.

The inhalation valve 66 is designed as a one-way valve or non-return valve. To this end, the inhalation valve 66 can make possible a flowing-in of the ambient air 18 through the inhalation valve 66 and/or can prevent an exiting of air or aerosol 3 through the inhalation valve 66.

The opening 70 of the discharge nozzle 2 is preferably arranged downstream from the valve body seat 72 and/or a valve plane that is formed by the valve body seat 72. In this way, it can be achieved that the aerosol 3 is applied only after passage of the air 18 through the inhalation valve 66, and consequently no aerosol components condense on the valve element 67.

It is further preferred that the discharge direction of the discharge nozzle 2 be at least essentially identical to a main direction of flow of the air 18 from the inhalation valve 66. In particular, the discharge direction of the discharge nozzle 2 and the main direction of flow of the air 18 from the inhalation valve 66 are parallel and/or coaxial, in particular relative to the longitudinal axis L. In this way, an especially efficient aerosol transport is ensured.

The stop 71, preferably formed by the intake opening of the chamber 6, preferably corresponds in shape and diameter to the inner edge 69 of the valve element 67. In this way, an especially uniform flow wall 73 can be achieved, ensuring that eddies and eddy-induced precipitate of aerosol components can be avoided.

According to an aspect of this invention, the stop 71 is formed by an edge of an intake opening 85 of the chamber 6. This advantageously makes possible continuous flow guidance and flow forming of the air 18 in the flow through the inhalation valve 66 into the chamber 6.

The intake opening 85 of the chamber 6 can have a section that conically narrows in the opening direction. The conically-narrowing section is preferably designed to be free-standing or forms a collar-shaped extension of the chamber 6, which can end in the intake opening 85.

The outer edge 68 of the valve element 67, the inner edge 69 of the valve element 67, the valve body seat 72, the collecting device 74 and/or the stop 71 can be designed at least essentially annular and/or can be arranged with one another in such a way that the focal points or geometric foci lie on a common axis, in particular the longitudinal axis L of the inhaler 1. The longitudinal axis L preferably corresponds to the linear direction of movement of the pump device 24 and/or the discharge direction of the discharge nozzle 2.

The inhalation valve 66 can have a fastening element 77 for circumferential fastening of the valve element 67, in particular on its outer edge 68. The inhalation valve 66 can furthermore have a clamping ring 78 for clamping the valve element 67 to the fastening element 77. In particular, the valve element 67 is thus clamped between the fastening element 77 and the clamping ring 78. The valve element 67 can also, however, be connected preferably snugly with the fastening element 77 in another way or can be fastened to the latter, in particular by an adhesive connection. A frictional connection by means of the clamping ring 78 is preferred, however.

By the fastening element 77, the clamping ring 78 or in another way, the valve element 67 can be clamped or pre-tensioned against the valve body seat 72. The valve element 67 thus snugly rests in a rest position or without the application of force on the valve element 67 preferably on the valve body seat 72. This can be achieved, on the one hand, by clamping or gripping, as an alternative or in addition also by the shape or internal stress of the valve element 67 or in another way. In the illustrated embodiment, the inhalation valve 66 is designed with pre-tensioning in the closed position. However, other design solutions are also possible.

The inhaler 1 can have incoming air openings 79, in particular on the intake side or upstream from the inhalation valve 66. These openings 79 make possible a flow of ambient air 18 to the intake side of the inhalation valve 66. In particular, the incoming air openings 79 are formed by through openings of the housing 14.

The fastening element 77, the collecting device 74, and/or the valve body seat 73 can be connected to one another via at least one arm, in particular can be formed in one piece.

According to another aspect of this invention that can also be achieved independently, the inhaler 1 has a respiration indicator 80, which has a wall section 81 of a chamber wall 82 that forms the chamber 6 or is formed in this way. In this case, the wall section 81 is designed to indicate a respiratory activity by deforming and/or movement. In particular, the respiration indicator 80 is designed to indicate a pressure differential between the inside space and the surrounding area of the chamber 6.

The wall section 81 can be designed to be expandable, flexible, deformable, curved, dome-shaped and/or membrane-like. In this way, it is made possible that comparatively small pressure differentials also lead to a deforming or movement in order to indicate the respiratory activity. In contrast to the chamber 6, the respiration indicator 80 can preferably be nontransparent, translucent, or opaque. This facilitates the reading.

The wall section 81 can be designed to be at least partially deformed in the shape of a vault or dome or curved in another way under the action of breathing in, out or through the chamber 6. In this case, a peak 83 or vault can be formed, in particular by a pressure differential acting on the wall section 81 between the inside space and surrounding area of the chamber 6 and the wall section 81 thus being deformed in a corresponding way.

Under the action of breathing out or through the chamber 6, the peak 83 can be facing the inside space of the chamber 6. Starting from a rest position of the wall section 81, a concave deforming is thus formed. In this case, it has to be taken into consideration that the chamber 6 preferably has rounded walls, a concave deforming of the wall section 81, i.e., especially already present if a convex basic shape is at least partially compensated for. Especially preferred, however, is a deforming in the intake from or through the chamber 6 or in the case of underpressure in the chamber 6 relative to the surrounding area, in which as a result, the concave deforming also leads to a concave surface in the area of the wall section 81.

The wall section 81 is preferably designed in such a way that under the action of breathing in the chamber 6 or in the case of overpressure in the chamber 6 relative to the surrounding area, it is convexly deformed or curved or deformed or curved in such a way that the peak 83 is formed on a side facing away from the inside space of the chamber 6. In this case, it can be provided that the convex deforming forms in an already convex basic shape in a rest position or the like of the wall section 81, i.e., a convex basic shape is curved in a more convex manner by the convex deforming.

However, other forms of a deviation of the wall section 81 are also possible, which under the action of breathing out or through the chamber 6 or in the case of underpressure in the chamber 6 is directed to the inside space of the chamber 6, and/or which under the action of breathing in the chamber 6 or in the case of overpressure in the chamber 6 relative to the surrounding area is directed toward the outside or in a direction facing away from the inside space of the chamber 6.

It is thus preferred that the wall section 81 can be deflected or deviated at least partially under the action of breathing in, out, and/or through the chamber 6, The deflection or deviation is carried out preferably by material deforming or material expansion. The latter is preferably carried out elastically or reversibly, so that an indication of respiratory activity can be implemented in multiple ways. A material deforming or material expansion or other movement or deviation of the wall section 81 is preferably more than 0.5 mm, in particular more than 1 mm or 2 mm, in the illustrated embodiment more than 3 mm, and/or less than 20 mm, preferably less than 15 mm, and in particular less than 10 mm. Such a material deforming or material expansion or other deviation is optically readily detectable. Too large material expansion can, however, result in the formation of volume differences of the chamber 6 or in an influencing of the flow characteristic of the chamber 6 by changing the flow wall. Disruptions of the flow path can result in an increased deposition of aerosol components on the chamber wall 82, i.e., in a loss of active ingredient.

The wall section 81 can have multiple stable states. In particular, the wall section 81 can occupy (only) two stable states, in which the wall section 81 is curved in each case. For example, the wall section 81 can have a material excess increasing inward or a curved basic shape. If the shape of the wall section 81 is compensated for by exerting a force, for example by a pressure differential, the wall section 81 turns into a reverse shape. Such an unstable or changing behavior offers the advantage that a strong movement of the change can readily be detected by eye over a comparatively short time. As an alternative or in addition, an acoustic signal or the like can also be generated by a change in the shape direction. As an alternative or in addition, the respiratory sensor 80 can thus acoustically signal respiration.

The wall section 81 is thus preferably designed to turn or to change from a concave to a convex shape or vice versa, preferably under the action of breathing in, out, or through the chamber 6 or by the pressure differential that acts on the wall section 81. The inhaler 1 is preferably designed so that in the case of an intake process in the chamber 6 relative to the surrounding area, an underpressure results, which is considerably greater than 0.2 hPa, preferably greater than 0.5 hPa, and in particular greater than 1 or 2 hPa. As an alternative or in addition, it is provided that the underpressure is considerably less than 10 hPa, preferably less than 5 hPa, and in particular less than 4 or 3 hPa. A pressure differential of more than 0.2 or 0.5 hPa is advantageous in order to make possible a sufficient deviation, deforming or movement of the wall section 81. In the case of an underpressure of more than 1 or 2 hPa, an indication of the respiratory activity is especially easy by a comparatively large deforming of the wall section 81. An underpressure of less than 10, 6 or 5 hPa is preferred since the underpressure accompanies a corresponding intake resistance for the patient or other user of the inhaler 1—a correspondingly lower underpressure than an effective and complete inhalation thus supports. An underpressure of less than 4 or 3 hPa is especially preferred. The wall section 81 is preferably designed to indicate the respiratory activity in the case of the described pressure differentials in particular via a shape. The shape or maximum deviation of the wall section 81 can lie in a range of between 0.5 mm and 20 mm in the case of the described pressure differentials.

The pressure differentials in an expiratory process can deviate from those under the action of breathing out or through the chamber 6. The inhaler 1 preferably has the inhalation valve 66, which automatically closes under the action of breathing in the chamber 6. The dispensing device 7 is preferably designed for use in a bodily orifice, in particular in a nose hole or nostril 9. Therefore, an expiratory process can be carried out by an alternative bodily orifice, such as another nose hole or the like. In the chamber 6, an overpressure or dynamic pressure results in such a case in an expiratory process in the chamber 6. The pressure differential adjoining the wall section 81 due to the dynamic pressure in the chamber 6 can be less than 50 hPa, preferably less than 40 or 30 hPa, and in particular between 5 and 15 hPa, relative to the surrounding area of the chamber 6. Therefore, it is preferred that the wall section 81 be designed to make possible a shape outward in the case of corresponding pressure differentials, which allow a non-destructive indication of a respiratory activity, in particular between 0.5 mm and 20 mm.

In one example, the wall section 81 can be designed so that under the action of breathing in the chamber 6, a noticeable shape of, for example, 1 to 5 mm results; the shape in an opposite direction during the intake process, i.e., under the action of breathing out or through the chamber 6, however, precipitates comparatively little and lies, for example, between 0 mm and 1 mm. As a result, however, even with such a configuration, the respiratory activity can be indicated, since at least the presence or absence of a deforming or movement can be detected. Thus, it may be enough that a movement and/or deforming can be detected by eye only in the case of an expiratory process, and a beginning intake process is indicated in that a deforming or movement of the wall section 81 is inferred.

In a method for administering a medication, in particular the aerosol 3 from the pharmaceutical agent preparation 4, the inhaler 1 is provided with the respiration indicator 80, whereby the inhaler 1 has the chamber wall 82 that forms the chamber 6 and a dispensing device 7, whereby the dispensing device 7 for fluidic connection of the chamber 6 to the bodily orifice is introduced or inserted into the bodily orifice, or is applied on the bodily orifice. Then, a patient can breathe through and/or in the inhaler 1. The respiration indicator 80, which has the wall section 81 of the chamber wall 82 or is formed in this way, is observed, and, depending on the deforming and/or movement of the wall section 81, the dispensing of medication, in particular the forming of aerosol, is triggered. It is a goal to start the forming of aerosol at the beginning of an intake process so that the aerosol 3 can be inhaled as quickly and completely as possible. For example, it is observed that the wall section 81 has a shape or peak that faces away from the inside space of the chamber 6, and a forming of aerosol is triggered as soon as this shape decreases or as soon as this shape disappears or changes. In this way, the forming of aerosol can be synchronized in an advantageous way with the intake process.

The pressure differential between the inside and outside of the chamber 6 can be determined decisively by cross-sections or fluidic properties of the inhalation valve 66 or the intake opening 85 of the chamber 6. As a whole, the inhaler 1 or the intake opening 85 of the chamber 6 is designed to exhibit flow resistance, by which under the action of breathing in, out, or through the chamber 6, an underpressure and/or overpressure can be generated in the chamber 6 relative to the surrounding area, by which the wall section 81 can be deformed and/or moved.

The ability to detect deforming or movement of the wall section 81 is supported by the respiration indicator 80 having an indicator means 84. The indicator means 84 can be designed to react with the deforming or movement of the wall section 81, in particular by a change in the color or color intensity, a change in the reflection or transmission properties relative to visible light, by (enhanced) movement, and/or acoustically. For example, a hologram can be applied to the wall section 81 that produces color and reflection changes even in the case of very small positional changes of areas of the wall section 81, which changes can be clearly detectable by eye even if the movement or deforming was difficult to detect as such with the naked eye. As an alternative, a pin or arm can be provided in the area of the wall section 81, and said pin or arm converts the deforming or movement of the wall section 81 into a more significant movement.

The wall section 81 can be inserted or is insertable, preferably by friction, into the chamber wall 82. Also, the wall section 81 can be connected snugly, in particular in an airtight or pressure-sealed way, with the chamber wall 82 and sprayed, bonded, welded or clamped on the chamber wall 82. As an alternative, the wall section 81 can also be formed by the chamber wall 82. A snug fastening of the wall section 81 to the chamber wall 82 has the advantage that the respiration indicator 80 according to the invention draws no secondary air, which would be disadvantageous for the transport of aerosol and furthermore could lead to active ingredient losses via eddying of the aerosol 3 guided into the chamber 6.

The respiration indicator 80, in particular the wall section 81, is preferably arranged outside of the flow, thus the air stream is preferably not impeded by the chamber 6 or the releasing of aerosol. The inhaler is preferably closed or designed to be airtight between the intake opening 85 of the chamber 6 and an outlet 10 of the dispensing device 7.

The wall section 81 and the chamber wall 82 can have different materials and/or material thicknesses. In this case, it is preferred that the material of the wall section 81 be more flexible, slightly more expandable, and/or thinner than the material of the chamber wall 82. This makes possible a movement or deforming of the wall section 81 by which respiratory activity can be indicated.

The wall section 81 can have a connecting means for fastening in a through passage 88 of the chamber wall 82. The wall section 81 can thus be inserted or is insertable into a through passage 88 of the chamber wall 82. Preferably, the wall section 81 has a frame 86, which can limit the wall section 81 and can have a contour that corresponds to a an end of the through passage 88 of the chamber wall 82.

The frame 86 or another connecting means is preferably designed for airtight and/or pressure-sealed connection of the wall section 81 with the chamber wall 82. As shown, e.g., in FIGS. 11-13, the connecting means can include an edge with a U-shaped cross section that is designed for encompass/receive the edge of the through passage in the chamber wall 82. As an alternative or in addition, the frame 86 can be bonded with the chamber wall 82.

The respiration indicator 80 is preferably arranged above or facing the user in a position of use of the inhaler 1. The inhaler 1 can be provided in particular for use with a horse 5. In this case, it is preferred that the dispensing device 7 be designed for use in a horse's nostril 9, whereby the position of use can relate to an inhaler 1 inserted into the horse's nostril 9. The respiration indicator 80 can be arranged above and/or on the right relative to the longitudinal axis L in the direction of flow of the inhaler 1, which can comply with the dispensing direction of the discharge nozzle 2. This enables an angle of observation, from which the movement of the wall section 81 is especially easy to observe.

The wall section 81 can have a surface area that is larger than 0.5 cm$^2$, preferably larger than 1 cm$^2$, in particular larger than 2 cm$^2$, and/or smaller than 25 cm$^2$, preferably smaller than 20 cm$^2$, and in particular smaller than 15 cm$^2$. In the case of a larger surface area of the wall section 81, greater deviations at the same pressure differential can be generated, which promotes a clearness of display of the respiration indicator 80. A very large wall section 81, however, leads to the fact that the flow geometry of the inhaler 1 can change based on the pressure differential between the inside space of the chamber 6 and the surrounding area, which at least in the case of more significant changes can lead to an increased condensation of the pharmaceutical agent preparation 4 from the aerosol 3. Furthermore, a very large wall section 81 can lead to instabilities of the chamber 6. The preferred values therefore represent a good compromise between the advantages and disadvantages that are connected with different surface areas of the wall section 81.

The wall section 81 can continue a jacket line or contour line of the chamber wall 82 adjoining the wall section 81 without a pressure differential between the inner and outer sides and/or can align with the chamber wall 82 adjoining the wall section 81. This makes possible an outside shape of the chamber 6 that is uniform in a state of rest without a pressure differential; this reduces susceptibility to contamination and furthermore is also aesthetically advantageous.

The wall section 81 can have a sealing surface for attachment to a boundary of the through passage 88, whereby the sealing surface is designed to be attached snugly to the boundary of the through passage 88 when inserting the wall section into the through passage 88.

In the case of an air-volume stream of between 300 l/h and 6,000 l/h, preferably between 600 l/h and 3,000 l/h, the inhaler 1 can be designed to generate a pressure loss or underpressure in the chamber 6 that is greater than 0.5 hPa, preferably greater than 1 hPa, in particular greater than 2 hPa, and/or less than 10 hPa, preferably less than 6 hPa, and in particular less than 4 hPa.

The wall section 81 can have an elastomer, latex, nitrile rubber, neoprene, polyurethane, styrene-ethylene-butadiene-styrene, styrene-butadiene rubber and/or silicone, or can be at least essentially formed therefrom. The wall section 81 can have a material—or be formed therefrom—which has an elasticity module of smaller than 0.1 kN/mm2, preferably smaller than 0.05 kN/mm2, and in particular smaller than 0.02 kN/mm2. In particular, the wall section 81 has a wall thickness that is less than 300 μm, preferably less than 200 μm, in particular less than 150 μm, and/or greater than 10 μm, preferably greater than 20 μm, and in particular, greater than 50 μm. In this way, a reliable display can be ensured.

The wall section 81 can be designed to generate a mechanical stress increasing disproportionately with increasing deviation or expansion. In this way, damage by overexpansion can be prevented.

The wall section 81 can be arranged at a distance from the outlet 10 and/or the intake opening 85 of more than 3 cm, preferably more than 4 cm, and/or less than 10 cm, preferably less than 8 cm. In this way, the respiration indicator 80 is also visible during use and, moreover, is arranged so that sufficient pressure differentials occur through the respiratory process.

The wall section 81 can have a main extension surface with a surface normal in the center relative to the main extension direction of the wall section, whereby the normal a) is crosswise, in particular perpendicular, to a main flow direction in the area of the wall section 81; b) is crosswise, in particular perpendicular, to a releasing direction of the discharge nozzle 2; and/or c) encompasses an angle in a spraying in a main flow direction in the area of the wall section 81 and/or in a spraying in the releasing direction of the discharge nozzle 2, of the inhaler 1 with a releasing direction in the area of the outlet 10 of the adapter, which angle is more than 30°, preferably more than 40°, in particular more than 45°, and/or less than 80°, preferably less than 70°, and in particular less than 65°. Surprisingly enough, it has been shown that at such a position, visibility and function are optimal.

According to another aspect of this invention, the respiration indicator 80, in particular the wall section 81, can be used for a sealing test. In this case, the inside space of the chamber 6 can be tensioned starting from the dispensing device 7. The inhalation valve 66 can close in such a case. The overpressure that forms can, also independently of a respiratory process, be indicated by the respiration indicator 80. In this way, a sealing test or the like can be performed.

The sealing test can serve in particular to check for adequate sealing between the chamber 6 and the dispensing device 7, between the chamber 6 and the housing 14, and/or between the housing 14 or the chamber 6 and the inhalation valve 66. In this case, the inside space formed by the chamber 6 and/or the dispensing device 7 can be tensioned and closed. An overpressure that is generated in this way can be indicated by the respiration indicator 80. A pressure loss can be indicated in particular by the movement or deforming of the wall section 81. In this way, a leak, which leads to a pressure loss, can be indicated by the respiration indicator 80 or the wall section 81.

According to another aspect of this invention, the respiration indicator 80 can be designed in a continuous display of the respiratory activity and/or pressure change between the inside space of the chamber 6 and the surrounding area. In particular, breathing in, out, and/or through the chamber 6 leads to a continuous pressure fluctuation corresponding to the respiratory activity. Such a continuous pressure fluctuation can advantageously be indicated continuously by the respiration indicator 80 according to the invention. In this way, it is possible to differentiate in an advantageous way between multiple sections, in addition to the respiratory direction, even within the intake and expiratory phases. This makes possible an especially exact determination of a triggering time. As an alternative or in addition to this, the respiration indicator 80 can be designed to indicate respiratory activity analogously, in particular by a deviation, position and/or deforming that is/are at least essentially continuous and/or correspond(s) to the pressure differential between the inside space and the surrounding area of the chamber 6. However, other solutions are also possible.

The different aspects of this invention can be achieved both individually and combined. In particular, the tensioning mechanism 28 can also be realized for triggering an MDI or independently by an SMI. Furthermore, the inhalation valve 66 can also be used for other purposes beyond the inhalers and can be realized individually. The indicator 48 according to the invention can likewise also be realized individually and independently for displaying already released or still available pharmaceutical doses, preferably in combination with a triggering mechanism. The same is true for the respiration indicator 80, which can also be integrated in a wall of other devices. Synergistic effects result in particular in a combination of the tensioning mechanism 28, triggering concept and/or indicator 48 with a metering ring 50 owing to the resource-conserving multiple use of components.

FIG. 14 shows the respiration indicator 80, according to the invention, in a variant of the manner in which the respiration indicator 80 is preferably connected to the chamber 6 in a resting manner. In FIG. 14, the respiration indicator 80 is shown in the rest position. As the rest position, reference is preferably made to a state of the respiration indicator 80 in which the internal pressure corresponds at least essentially to the ambient pressure of the chamber 6. In the rest position, the wall section 81 is preferably at least essentially level or flat.

FIG. 15 shows the deviation of the wall section 81 in the case of overpressure in the chamber 6, breathing in the chamber 6 and/or in expiratory position. FIG. 16 shows the deviation of the wall section 81 in the case of underpressure in the chamber 6, with breathing out or through the chamber 6 and/or in the inhalation position.

The respiration indicator 80 is designed to signal breathing in, out and/or through the chamber 6 by display of the pressure differential between the inside space and the surrounding area of the chamber 6. In this connection, in addition to the explanations, further reference is made to FIGS. 11 to 13. The features and properties of the respiration indicator 80 from FIGS. 14 to 16 preferably correspond to those previously explained in connection with FIGS. 11 to 13 and vice versa. In particular, the respiration indicator 80 from FIGS. 14 to 16 can also have an indicator means 84.

It is preferred that the chamber 6 be deformable only in the area of the wall section 81 by respiratory activity. Preferably, the chamber 6 is predominantly or at least essentially dimensionally stable. In particular, the chamber wall 82 predominantly or at least essentially is stable so that a deforming of the chamber 6 or the chamber wall 82 is prevented by differential pressures between the inside space and the surrounding area of the chamber 6, which can be realized under the action of breathing.

The at least essentially dimensionally-stable part of the chamber 6 preferably has the through passage 88. The through passage 88 is preferably sealed airtight by the wall section 81. The wall section 81 is, as already explained previously, preferably flexible in such a way that breathing that is done in, out or through the chamber 6 or a pressure differential realized in this way between the inside space of the chamber 6 and the surrounding area of the chamber 6 results in a preferably visible deforming of the wall section 81.

The wall section 81 or a part thereof that can be deformed by respiratory activity preferably has a surface area that is less than 20%, preferably less than 15%, in particular less than 10% of the surface area of the chamber wall 82 and/or the surface of the chamber 6. It is preferred that the chamber 6 be more than 80%, preferably more than 85%, and in particular more than 90% dimensionally stable. The wall section 81 preferably comprises less than 20% or 15%, in particular less than 10%, of the chamber wall 82 that forms the chamber 6. In this way, it can be avoided in an advantageous manner that the flow geometry of the inside space of the chamber 6 is influenced under the action of the respiratory activity in, from or through the chamber 6.

It has been shown that, in the case of deformability of larger areas of the chamber wall 82, the flow properties of the chamber 6 depend on the respective position of the chamber wall 82. As a consequence, an increased or non-reproducible amount of pharmaceutical agent preparation 4 condenses on the chamber wall 82 and consequently is not released. In the case of the approach according to the invention, in which only the wall section 81 is deformable and the wall section 81 occupies only a small portion of the entire chamber wall 82, the flow geometry of the chamber 6 is at least essentially independent of the deforming of the wall section 81. This advantageously results in low and reproducible active ingredient losses and consequently in an exact, reliable and reproducible metering.

In FIGS. 14 to 16, the respiration indicator 80 or the wall section 81 according to the invention is held in a resting manner on the chamber 6. To this end, the chamber 6 in the illustrated embodiment has a connecting section 87, to which the wall section 81 can be clipped or locked. The connecting section 87 preferably surrounds the through passage 88, in particular continuously. In the illustrated embodiment, the connecting section 87 surrounds the through passage 88 of the chamber 6 in an annular and/or frame-like manner. The connecting section 87 is preferably designed to be in the form of a flange or socket. The connecting section 87 is preferably molded-on or in with the chamber wall 82 or formed in one piece with the chamber wall 82. Here, in principle, however, other solutions are also possible, for example a connecting section 87 that is screwed, glued or welded to the chamber 6 or connected to the chamber 6 in some other way.

The connecting section 87 preferably comprises an undercut or indentation 89. The undercut or indentation 89 is preferably designed to hold the wall section 81 in a particularly positive, non-positive and/or resting manner. In the illustrated embodiment according to FIG. 14, the wall section 81 is engaged in the undercut or indentation 89. In this way, the wall section 81 can be held on the chamber 6 and/or connected to the chamber 6.

Alternatively or additionally, the wall section 81 is bonded, in particular glued, welded, formed and/or molded, to the chamber 6. Preferably, the wall section 81 is bonded to the connecting section 87. The wall section can be bonded to the wall section 81 and/or the chamber 6 at the connecting section 87 or the undercut or indentation 89.

Gluing the wall section 81 to the chamber 6 can provide advantages regarding a flexible or elastic connection, which can be non-permanent or detachable. Welding the wall section 81 to the chamber 6 can provide advantages regarding a very durable, permanent connection. Forming or moulding the wall section on the chamber 6 can provide advantages regarding a durable and reliable airtight connection, where providing the undercut or indentation 89 does not need to be provided.

Particularly preferably, the wall section 81 is bonded to the chamber 6 and/or to the connecting section 87 and/or to the undercut or indentation 89 in addition to a form fit of the wall section 81 with the chamber 6 and/or to the connecting section 87 and/or to the undercut or indentation 89. This enables an even more reliable and durable connection.

Preferably, the chamber 6 and/or the connecting section 87 comprising a projection 91. The projection 91 surrounds the through passage 88 preferably on a radial outer side. In this case, the projection 91 preferably forms a bead that is directed radially outward and/or that extends preferably continuously. The projection 91 preferably forms the undercut or indentation 89. As an alternative or in addition, however, the undercut or indentation 89 can also be formed by one or more locking catches or in some other way. The forming of the undercut or indentation 89 by the projection 91, in particular the projection 91 that runs continuously around the through passage 88, offers the advantage, however, of a secure fixing of the wall section 81 while achieving good sealing action simultaneously.

In the illustrated embodiment of FIG. 14 to FIG. 16, the wall section 81 is clipped or locked to the connecting section 87 or positively held in some other way on the connecting section 87. A fastening section 90 of the wall section 81 preferably engages in the connecting section 87 or the undercut or indentation 89. In this way, the wall section 81 can be held in a secure and airtight manner on the chamber 6 in an advantageous way.

The connecting section 87, in particular the projection 91, is preferably encompassed by the fastening section 90 of the wall section 81. In this way, a preferred airtight clipping or locking connection between the wall section 81 and the other chamber wall 82 can be realized.

The clipping or locking of the wall section 81 to the connecting section 87 of the chamber 6 offers the advantage of a simple assembly and interchangeability of the wall section 81. In particular, a defective wall section 81 can also be interchangeable in an advantageous way by the end-user on the spot.

The wall section 81 preferably comprises an elastic material, impermeable material or rubber-like material or is comprised thereof. Preferably, the wall section 81 in the fastening section 90 has a higher material strength than in an area overlapping the through passage 88. In this way, a more reliable holding of the wall section 81 can be ensured.

Figure 20:
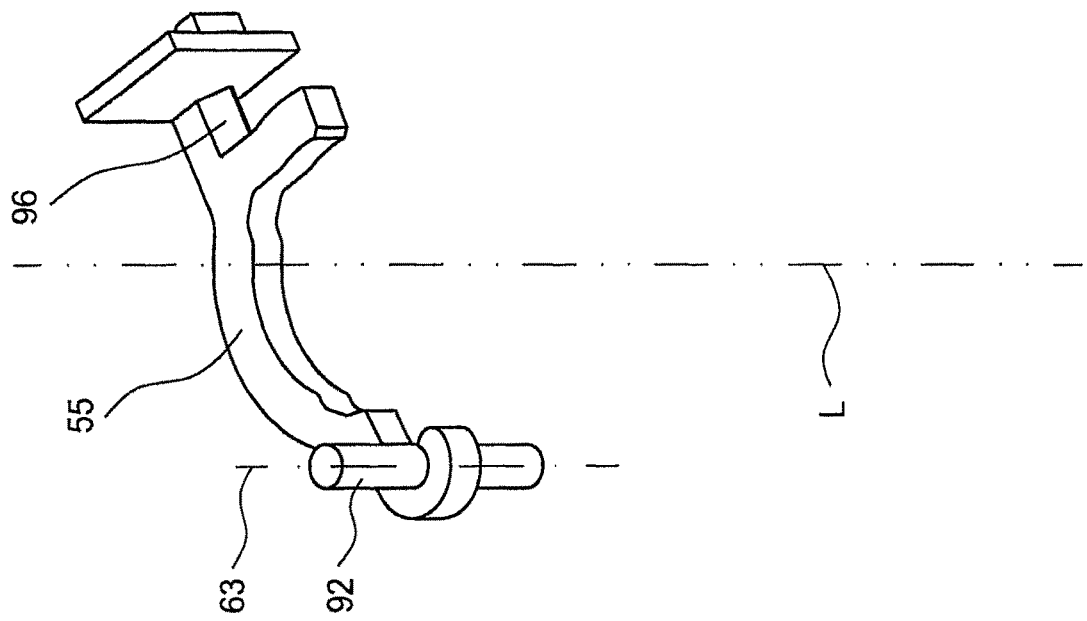
FIG. 20 is a perspective view of a pivot arm of the inhaler in accordance with the second embodiment.
Figure 19:
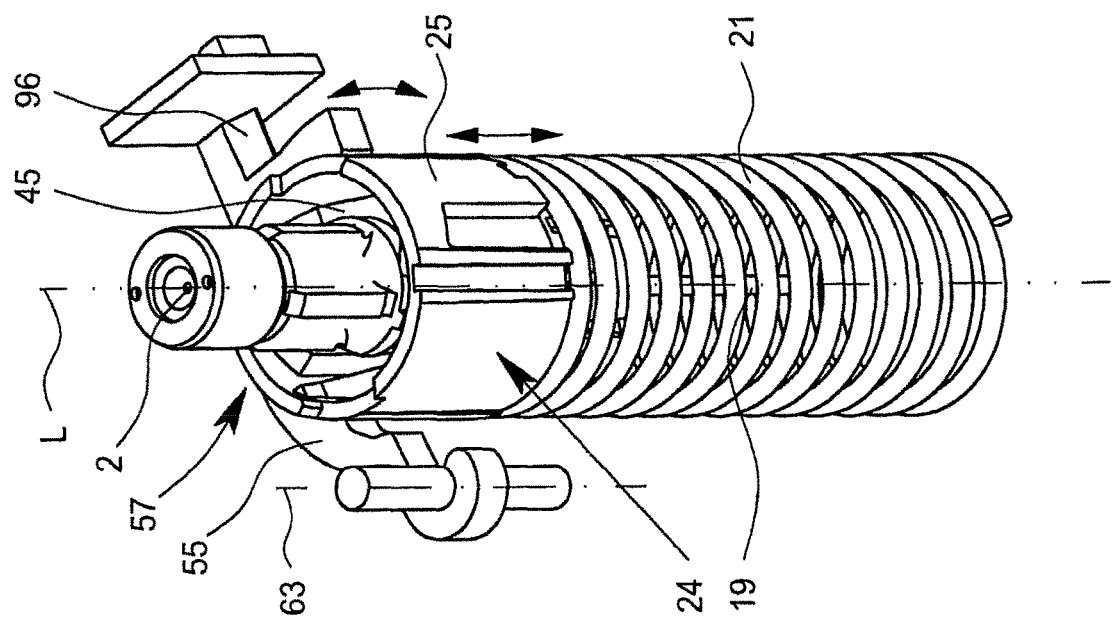
FIG. 19 is perspective view of the tensioning device of the pressure generator in accordance with the second embodiment.

FIGS. 17 and 18 show a view of a pressure generator 20 and the actuating lever 26 of the inhaler 1 according to another embodiment. In FIG. 19, the pressure generator 20 is shown with the pivot arm 55. FIG. 20 shows the pivot arm 55 without the pressure generator 20. FIGS. 21 to 24 show views of the pressure generator 20 with the actuating lever 26 in different positions.

Hereinafter, only essential differences and characteristics are dealt with in comparison to the above-explained inhaler 1. Components that are not depicted or not depicted in detail are preferably realized as explained above. This also applies for the indicator 48, which is not provided in the variant according to FIGS. 17 to 24, but can be realized as described above. In a corresponding way, a combination with one or more of the various above-described aspects and features is possible and advantageous.

The inhaler 1, according to the invention, is preferably designed to be operable with only one hand. This has the advantage that the second hand of an operator is available for other activities, in particular holding a horse 5.

An aspect of this invention that can also be achieved independently relates to an inhaler 1, preferably for insertion into a nostril 9, in particular a nostril of a horse 5, with a pressure generator 20 that can be driven by a tensioning device 21 for discharging a pharmaceutical agent preparation 4, whereby the tensioning device 21 can be tensioned by movement of a tensioning part, in particular the actuating lever 26, from a first position of the tensioning part into a second position of the tensioning part, whereby the inhaler 1 is designed to block the discharge of the pharmaceutical agent preparation 4 and to produce the discharge of the pharmaceutical agent preparation 4 after movement of the tensioning part from the second position back into the first position by a repeated movement of the tensioning part from the first position in the direction of the second position.

The above-mentioned aspect relates to the use of the tensioning part, which is also used for tensioning the tensioning device 21, for triggering. It surprisingly has been shown, that the use of the same part for tensioning and triggering enables a very sturdy and resource-preserving design. In particular, no knobs that are small and thus difficult to operate under adverse conditions or sensitive parts or the like are necessary.

The tensioning part preferably is configured such that a force F is introducible into the tensioning part. In particular, the tensioning part has a grip portion, a handle or part for manual operating the tensioning part. The tensioning part preferably is adapted to forward or introduce the force F acting on the tensioning part for tensioning the tensioning device 21.

Alternatively or additionally, the tensioning part can be adapted to prepare or enable discharging the pharmaceutical agent preparation 4. Alternatively or additionally, the tensioning part can be adapted to prepare the inhalator 1 or the pressure generator 20 and/or the pump device 24 for discharging the pharmaceutical agent preparation 4.

The tensioning part preferably is movable, relocatable and/or slidable, preferably repeatedly. The tensioning part preferably is movable, relocatable and/or slidable, whereby the tensioning device 21 is tensioned and/or the inhaler 1, the pressure generator 20, the pump device 24 and/or discharge of pharmaceutical agent preparation 4 is triggered and/or driven.

The tensioning part is especially preferably realized by the actuating lever 26, since the latter enables both the above-explained advantages relative to the tensioning process as well as a precise control of the triggering even under rough environmental conditions. As an alternative or in addition, the tensioning part can also be realized as a knob, switch, rocker or as some other movable part.

The tensioning part, in particular the actuating lever 26, is preferably pre-tensioned in the first position, in particular the rest position, also called the resting position. In the illustrated embodiment, the reset element 47 brings about the reset into the first position and/or the pre-tensioning into the first position. The reset element 47 is a spring, in particular a compression spring and/or a spiral spring in the illustrated embodiment of FIGS. 17 to 24.

In the embodiment of FIGS. 17 to 23, the triggering device 27 preferably comprises the tensioning part. It is preferred that the triggering device 27 be designed to enable a triggering process only in the case of a tensioned tensioning device 21. When the tensioning device 21 is untensioned or only pre-tensioned, the triggering device 27 preferably prevents a triggering. The triggering device 27 is thus preferably designed to enable or to prevent the triggering as a function of a tensioning state or a preparation or suitability for triggering and/or for discharging the pharmaceutical agent preparation 4.

The triggering is preferably prevented when and/or as long as the tensioning device 21 has not yet reached a preset tensioning state or the inhaler 1 is not ready or prepared in some other way for discharging the pharmaceutical agent preparation 4. In particular, the triggering is prevented when and/or as long as the tensioning device 21, the pressure generator 20, the pump element 24 and/or the holder 25 is/are not yet blocked or is/are secured against triggering.

The triggering by means of the tensioning part is preferably enabled when the tensioning of the tensioning device 21 reaches a preset tensioning, the inhaler 1 is prepared for administering the pharmaceutical agent preparation 4, and/or when a blocking of the pressure generator 20, in particular the pump device 24 or the holder 25, is carried out.

The triggering of the pump process, the pressure generation and/or the discharge of the pharmaceutical agent preparation 4 is preferably carried out after the tensioning process is concluded. Preferably, the triggering is carried out only after tensioning the tensioning device 21 by moving the tensioning part from the first position, in particular a rest position, in an actuating direction and after the tensioning part returns opposite the actuating direction into the first position with repeated movement in the actuating direction.

It is preferably provided that the triggering by movement of the tensioning part, in particular from the first position, is carried out up to a trigger point.

The distance over which the tensioning part can be moved up to the trigger point is preferably smaller than the distance that the tensioning part must be moved in the actuating direction in order to tension the tensioning device 21 completely and/or to block the pressure generator 20, the pump device 24 and/or the holder 25. The distance up to the trigger point, at which the tensioning part induces the triggering, is preferably less than 50%, preferably less than 40% or 30%, in particular less than 20%, or 15% of the distance of the tensioning device up to a point at which the tensioning device 21 is completely tensioned. In this way, a quick triggering can be ensured, since triggering does not require switching hands or any major movement.

Hereinafter, the aspect of the triggering based on FIGS. 21 to 24 is explained in more detail, in which different movement states of the triggering device 27 are depicted. Furthermore, the invention is hereinafter explained in more detail with the tensioning lever 26 as a tensioning part. The basic idea can, however, be transferred to other tensioning part.

In particular, as already explained above in connection with FIGS. 6 and 7, the pivot arm 55 blocks the pressure generator 20, in particular the pump device 24 and/or the holder 25, preferably in a positive manner and preferably when the tensioning process of the tensioning device 21 is concluded. To this end, the pump device 24 or the holder 25 is moved axially, preferably first against a force realized by the tensioning device 21, until the pivot arm 55 reaches the positive device 57, in particular an edge or a projection of the pump device 24 or the holder 25. In this way, the tensioning device 21 is tensioned. The energy stored in the tensioning device 21 can drive the pressure generator 20, preferably a mechanical pump mechanism for discharging the pharmaceutical agent preparation 4.

The pivot arm 55 is preferably clamped or pre-tensioned against the pump device 24 or the holder 25. As can be seen from FIGS. 17 and 18, the pivot arm 55 can be pre-tensioned with a pre-tensioning device 93, in particular a (tension) spring, against the pump device 24 and/or the holder 25, cf. also FIG. 19.

As soon as the pivot arm 55 reaches the positive device 57, the pump device 24 or the holder 25 by the tensioning process, the pivot arm 55 preferably automatically forms a positive fit with the positive device 57. Preferably, the forming of the positive fit is carried out by the pre-tensioning or clamping of the pivot arm 55. In this way or in another way, the pivot arm 55 is flush with the positive device 57 or the edge of the pump device 24 and/or the holder 25. In this way, an axial movement brought about by the tensioning device 21 or pump movement of the pump device 24 or holder 25 is blocked. As an alternative or in addition, however, it can also be provided that the pivot arm 55 engages in a recess or some other positive device 57 in such a way that the discharge of the pharmaceutical agent preparation 4 is blocked. In principle, other forms of blocking the pressure generator 20 at the end of the tensioning process are also possible, for example by a lock and/or frictional connection.

A position of the pivot arm 55, in which an axial movement brought about by the tensioning device 21 or pump movement of the pump device 24 or holder 25 is blocked, is also referred to hereinafter as a blocking position. A position of the pivot arm 55, in which the axial movement brought about by the tensioning device 21 or pump movement of the pump device 24 or of the holder 25 is released, is referred to hereinafter as a release position. It is thus preferred that the pivot arm 55 is moved into the blocking position at the end of the tensioning process and into the release position for triggering the administration of the pharmaceutical agent liquid 4. The release position is preferably a starting position from which the pivot arm 55 is moved into the blocking position after an initial or repeated tensioning process.

A movement of the pivot arm 55 back into the release position releases the drive of the pump device 24 or the holder 25 by the tensioning device 21. Subsequently, the pressure generator 20 can be driven by means of the tensioning device 21. As soon as the pivot arm 55 releases the drive of the pump device 24 of the holder 25 by the tensioning device 21, the tensioning device 21 shifts the pump device 24 or the holder 25 axially, preferably exclusively by spring force or clamping force.

The pivot aim 55 is preferably held on a shaft 92 and/or mounted to pivot (cf. FIGS. 19 and 20). The shaft 92 is depicted only in sections in FIG. 20 and preferably in a stationary manner, in particular connected to the housing 14, the housing section 42, or a receptacle for the pressure generator 20, molded thereon or formed in one piece.

The pivot arm 55 is preferably mounted to pivot on the shaft 92. As an alternative or in addition, the pivot arm 55 can be designed to embody a linear movement. In particular, the pivot arm 55 can also be movable by a (partial) linear movement or shifting in the blocking position and/or in the release position. The pivot arm 55 is preferably designed to block a pressure generation with the pressure generator 20, in particular an axial movement of the pump device 24 or the holder 25, preferably as already explained above.

In the embodiment according to FIGS. 17 to 24, the movement of the pivot arm 55 is carried out in the release position; the release and/or the triggering of the discharge of the pharmaceutical agent preparation 4 is/are preferably carried out by the actuating lever 26.

Figure 4:
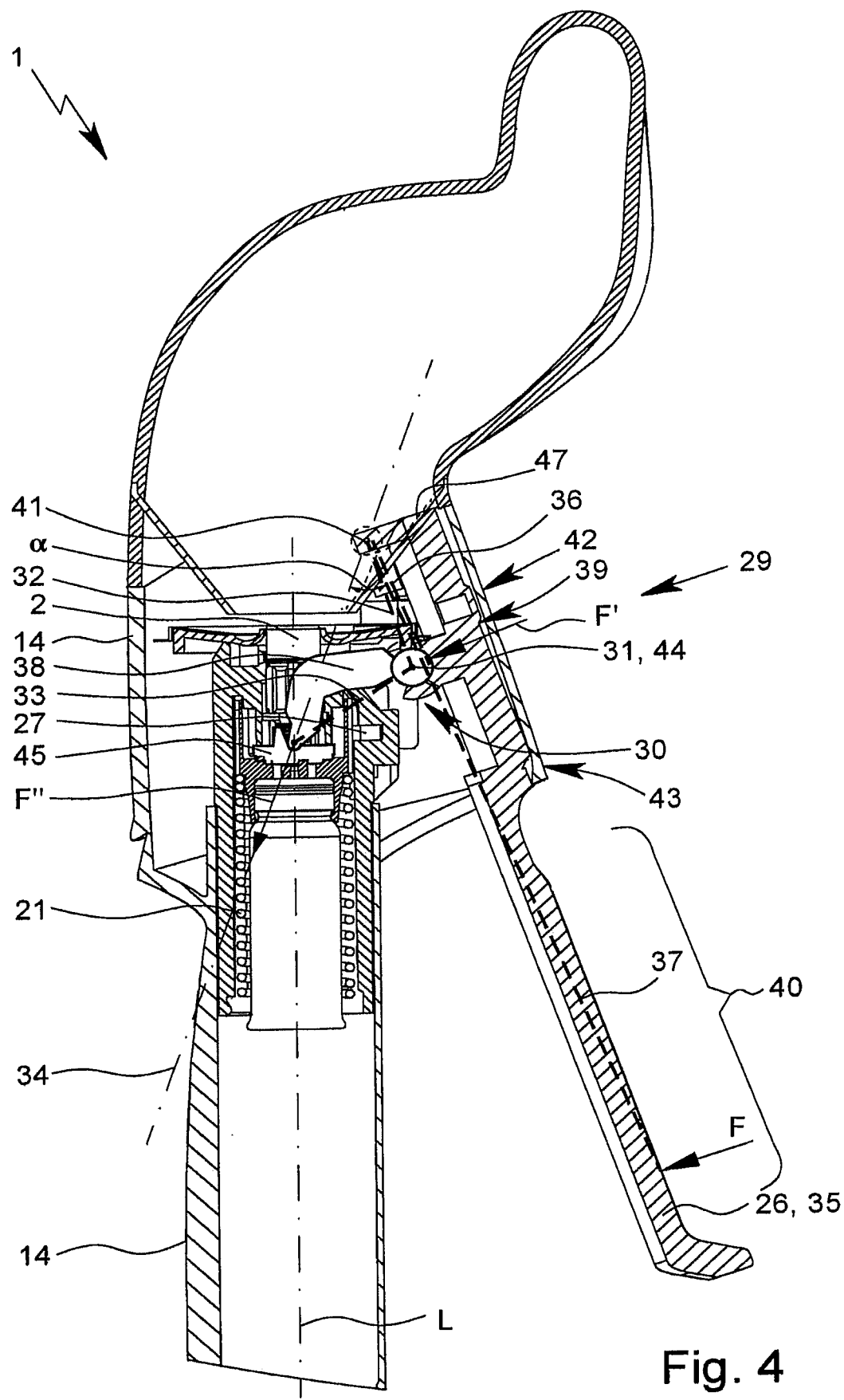
FIG. 4 is a sectional view of the inhaler in the area of the lever gear in the rest position.
Figure 5:
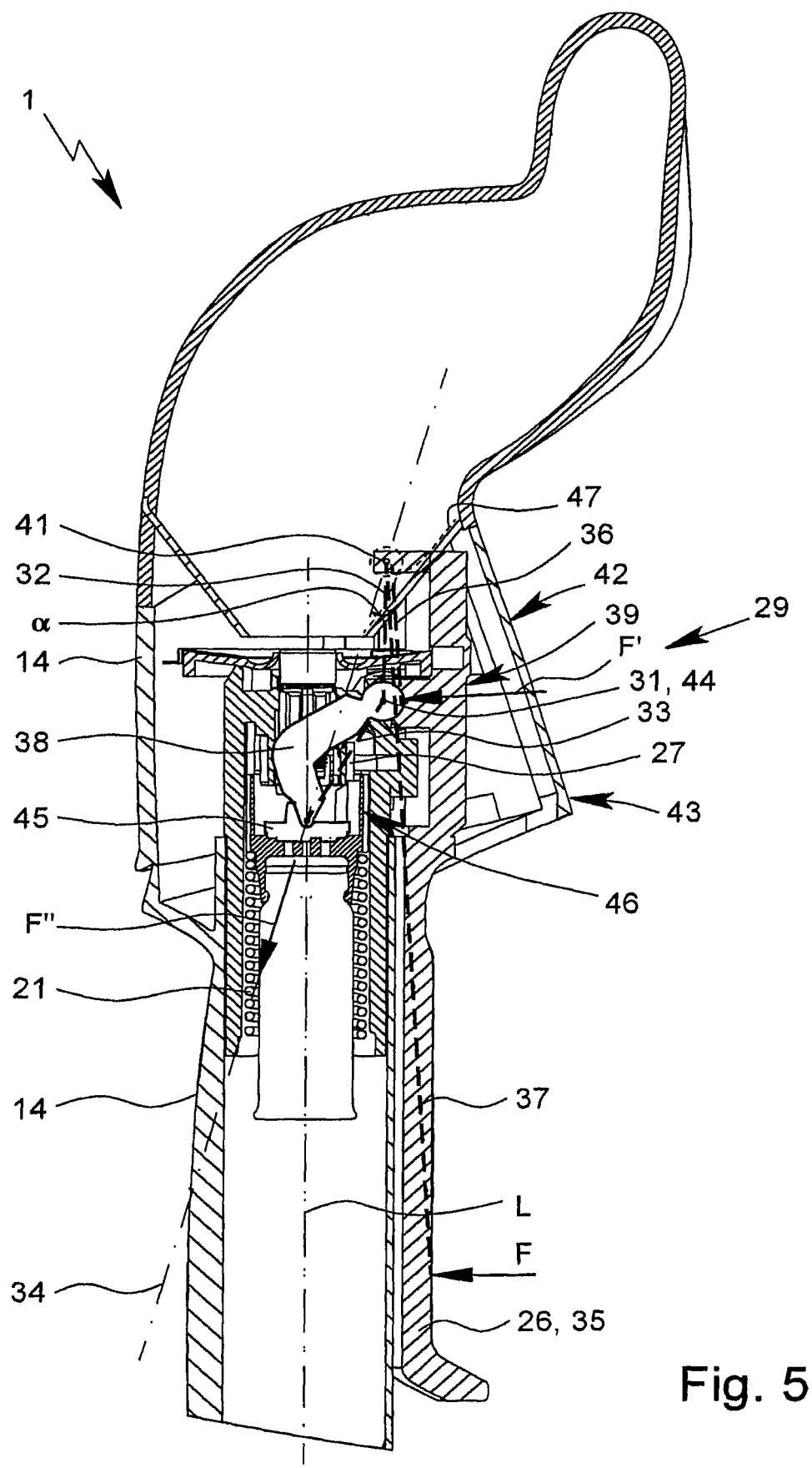
FIG. 5 is a sectional of the inhaler in the area of the lever gear in the tensioned position.
Figure 21:
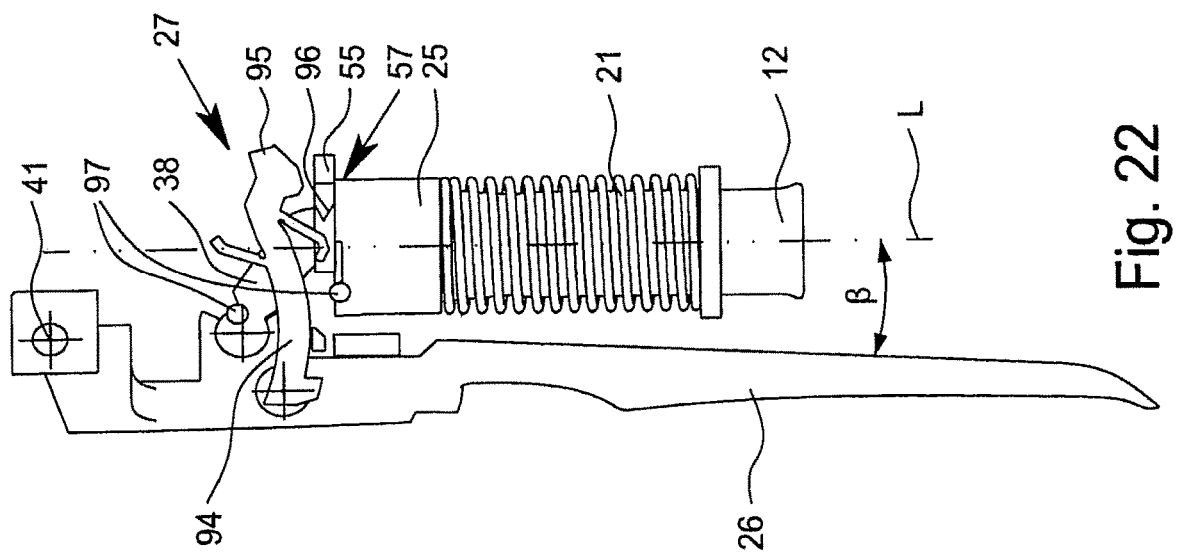
FIG. 21 is a view corresponding to that of FIG. 18 showing the pressure generator in accordance with the second embodiment with an actuating lever in the rest position.

In this connection, FIG. 21 shows the actuating lever 26 in the rest position, whereby the tensioning device 21 is untensioned or only pre-tensioned . In this starting state, the actuating lever 26 preferably projects from the housing 14 and/or forms a maximum pivoting angle α with the longitudinal axis L. To tensioning the tensioning device 21, the actuating lever 26 is moved in the direction of the housing 14 and/or moved in such a way that the pivoting angle α is reduced. In this way, the tensioning device 21 is tensioned, in particular as previously described in connection with FIGS. 4 and 5.

Preferably, a triggering mechanism 27 is provided, which has a triggering element 94. The triggering element 94 is preferably coupled to the actuating lever 26, in particular hinged on the actuating lever 26. The triggering element 94 is preferably a push rod.

The triggering element 94 preferably has an activating section 95 for moving the pivot arm 55 from the blocking position into the release position. In FIG. 21, the activating section 95 is located at a distance from a preferably wedge-like shifting area 96 of the pivot arm 55. Preferably, the triggering element 94 is guided in such a way that the activating section 95 does not move the pivot arm 55 during the tensioning process. As an alternative or in addition, the triggering element 94 is guided in such a way that the activating section 95 does not move the shifting area 96 or slides on the latter. In particular, at least one guide means 97 is provided, on which the triggering element 94 is guided in such a way that the activating section 95 runs past the pivot arm 55 or the shifting area 96. In this way, the pivot arm 55 can form the triggering blocker 46 with the triggering element 94. In the illustrated embodiment, the guide means 97 are formed by stationary elements, in particular pins. In FIGS. 17 to 24, the guide means 97 are shown only in sections for reasons of clarity.

Figure 22:
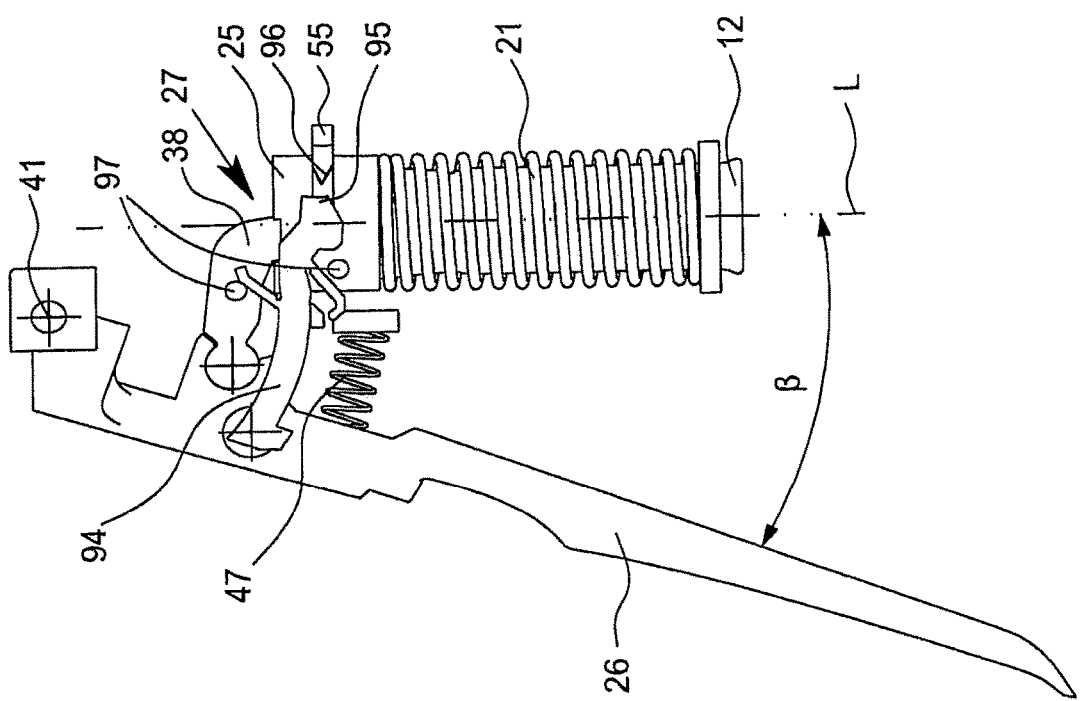
FIG. 22 is a view corresponding to that of FIG. 18 showing the pressure generator in accordance with the second embodiment with an actuating lever in the tensioned position.

FIG. 22 shows the end of the tensioning process. Preferably, at the end of the tensioning process, pivoting angle β, which encompasses the actuating lever 26 with the longitudinal axis L, is minimal. At the end of the tensioning process, the pivot arm 55 furthermore forms the positive fit with the positive device 57, which can be seen in FIG. 22 in such a way that the shifting area 96 and/or the pivot arm 55 is shifted in the direction of a center axis of the pump device 24 or the holder 25.

In FIG. 23, after the tensioning process is concluded, the actuating lever 26 is moved back into the position in which the actuating lever 26 preferably projects from the housing 14 and/or encompasses a maximum pivoting angle β with the longitudinal axis L. The pivot arm 55 is located in the blocking position, and the tensioning device 21 is tensioned . In the blocking position, the shifting area 96 is preferably brought toward the activating section 95, in particular in comparison to its position in the release position.

In FIG. 24, the pivot arm 55 has been shifted from the blocking position by the movement of the actuating lever 26 after the conclusion of the tensioning process from its blocking position in the direction of the release position. In this way, the drive of the pressure generator 20 is triggered with the tensioning device 21 and/or the administration of the pharmaceutical agent preparation 4.

It is preferred that when the pump device 24 begins to move, the pivot arm 55 is held in its release position. In the illustrated embodiment, the pump device 24 that slides along on the pivot arm 55 blocks the movement of the pivot arm 55 back into the blocking position. Here, however, other solutions are also possible.

Preferably, the triggering element 94 is guided in such a way that after the pivot arm 55 is moved into its release position, the activating section 95 is shifted relative to the shifting area 96 in such a way that the pivot arm 55 is prevented from moving beyond the release position. In particular, the triggering device 27 is designed in such a way that after reaching the release position of the pivot arm 55, the activating section 95 slides past the pivot arm 55 as the actuating lever 26 continues to move in the direction of the second position or in the triggering direction. In this way, in an advantageous manner, a high triggering sensitivity with simultaneous sturdy design is made possible, since damage of the pivot arm 55 is prevented.

Hereinafter, additional aspects and preferred configurations relating to the tensioning mechanism 28 are explained.

According to another aspect of this invention, the inhaler 1 comprises at least two levers 30, 35 designed for force multiplication.

Preferably, the inhaler 1 comprises a one-sided lever 35, which is designed for gear reduction and/or force multiplication and/or drives the elbow lever 30.

The lever gear 29 and/or the actuating lever 26 and/or the elbow lever 30 is/are preferably designed for force multiplication.

The lever gear 29 and/or the actuating lever 26 preferably increase(s) a force F that acts on the actuating section 40.

The lever gear 29 and/or the actuating lever 26 are preferably designed in such a way that a force F that acts on the actuating section 40 has an increased effect on the tensioning device 21 via the lever gear 29 and/or via the actuating lever 26.

The one-sided lever 35 preferably comprises a shorter lever arm 36, in particular as a load arm, and a longer lever arm 37, in particular as a force arm, preferably whereby the shorter lever arm 36 corresponds at least essentially to a lever arm 32 of the elbow lever 30.

The lever gear 29 is preferably designed in such a way that with a uniform force F that acts on the actuating section 40 with increasing deviation of the actuating lever 26 in the actuating direction, the force that acts on the tensioning device 21 increases. As an alternative or in addition, the lever gear 29 is designed to tensioning the tensioning device 21, preferably accomplished by a spring, in particular a compression spring, as the deviation of the actuating lever 26 increases in the actuating direction, whereby as the tensioning of the tensioning device 21 increases, the force that is to be exerted on the actuating section 40 of the actuating lever 26 or that is realized by the actuating section 40 of the actuating lever 26 decreases.

Preferably, the lever gear 29 comprises at least two levers, in particular the elbow lever 30 and the one-sided lever 35, or it is designed in at least two stages. In particular, the lever gear 29 is reduced in multiple stages, or the gear reduction ratio, i.e., the ratio between the drawn-off or resulting and fed force, in one or more stages, in particular each stage, of the lever gear 29 is greater than or equal to 1.

The one-sided lever 35 is especially preferably designed as the first stage of the lever gear 29, and the elbow lever 30 is designed as the second stage of the lever gear 29. However, other design solutions are also possible.

The one-sided lever 35 preferably produces a reduction gear or force multiplication of the force F that is fed by the user to the one-sided lever 35 and that acts on the inhaler 1, whereby the gear ratio of the one-sided lever 35 has in particular a constant value of greater than or equal to 1. Consequently, the force F' that is drawn off or that is caused by the one-sided lever 35 is preferably greater than or equal to the supplied force F.

The elbow lever 30 of a gear reduction or force multiplication especially preferably produces the force F' resulting because of the one-sided lever 35 or fed to the elbow lever 30. The gear ratio of the elbow lever 30 preferably increases with increasing actuation of the inhaler 1 or the actuating lever 26 and/or is greater with increasing tensioning of the tensioning mechanism 28 or the force multiplication. The gear ratio of the elbow lever 20 preferably is always greater than one. Preferably, the gear ratio increases with movement of the actuating lever 26 in the actuating direction.

The elbow lever 30 is preferably hinged on one end on the housing 14. The elbow lever 30 is preferably designed to introduce force on an end hinged on the housing via a hinge in the receptacle 45 and/or the pump device 24. The elbow lever 30 preferably produces a force component in the longitudinal direction L. The elbow lever 30 preferably directly produces a tensioning of the tensioning device 21. Preferably, the elbow lever 30, in particular directly, acts on the receptacle 45 connected in a rigid manner to the tensioning device 21.

The force F' resulting because of the one-sided lever 35 or the actuating lever 26 or acting on the additional tensioning mechanism 28, in particular the elbow lever 30, preferably corresponds to the force F on the actuating section 40 multiplied by the factor of the gear ratio of the one-sided lever 35.

The force F'" that results because of the elbow lever 30 or that acts on the tensioning device 21 preferably corresponds to the force F' that acts on the elbow lever 30, multiplied by the factor of the gear ratio of the elbow lever 30, preferably whereby the force F' corresponds to the force F multiplied by the factor of the gear ratio of the one-sided lever 35.

According to one aspect of this invention, the length of the one-sided lever 35, the lever arm 36, the lever arm 37 and/or the actuating lever 26 is variable, in particular adjustable. The longer lever arm 37 and/or the actuating lever 26 can preferably be folded out for further extension and/or via a hinge or like a telescope or can be extended in some other way.

Preferably, the actuating section 40 of the actuating lever 26 has a surface structuring for protection against sliding and/or an adhesive or rough surface. In particular, the actuating section 40 is provided with an elastic or flexible and/or rubber-like layer.

The tensioning mechanism 28 is preferably designed to tension the tensioning device 21 in the case of a movement of the actuating lever 26 from the rest position into the tensioned position.

The terms rest position and resting position and first position are preferably synonymous or interchangeable. Preferably, the terms tensioned position, pressure position, and second position are synonymous to one another or interchangeable. The rest position, resting position, first position and/or tensioned position, pressure position, and/or second position are preferably end positions.

In the case of a movement of the actuating lever 26 from the tensioned position back into the rest position, the tensioning device 21 preferably remains tensioned. By relaxing the tensioning device 21, preferably the pressure generator 20 is driven and/or the pharmaceutical agent preparation 4 is pumped and/or discharged. This is preferably carried out by a triggering and/or independently of the tensioning process.

Preferably, the actuating lever 26 can be swiveled between the pressure position/tensioned position/first position and the resting position/rest position/second position. However, other design solutions are also possible, in particular in which the actuating lever 26 can be moved in some other way relative to the housing 14. In particular, design solutions are possible in which the actuating lever 26 can be moved, preferably shifted and/or pressed, by means of a guide, in particular a linear guide, relative to the housing 14 between the pressure position/tensioned position/first position and the resting position/rest position/second position.

The lever gear 29, in particular the actuating lever 26, can preferably be locked, clamped or engaged in the tensioned position and/or in the resting position, for example for transport and/or in order to prevent an inadvertent actuation of the actuating lever 26. The one-sided lever 35 and/or its longer lever arm 37 is/are preferably formed between the pivot point 41 of the actuating lever 25 and the actuating section 40. The short lever arm 36 is preferably shorter than the long lever arm 37. Preferably, the long lever arm is more than twice as long as the short lever arm 36.

In a preferred embodiment, the pivot point 41 of the actuating lever 26 rests at least essentially on or in the vicinity of the longitudinal axis L of the inhaler 1. In particular, the pivot point 41 is less than 3 cm, preferably less than 2 cm, and in particular less than 1 cm from the longitudinal axis L and/or less than the length of the first lever arm 32 and/or the second lever arm 33 from the longitudinal axis L. In this way, the force F''' of the lever gear 29 that in particular acts on the pump device 24 acts at least essentially on the longitudinal axis L. In this way, in an advantageous manner, a good transmission of force to the pump device 24 and/or the tensioning device 21 can be achieved.

Preferably, the actuating lever 26 is mounted on two pivot points 41, in particular in the manner of a fork. In particular, the actuating lever 26 at least partially encompasses the chamber 6. In this way, a more compact inhaler 1 can be achieved. However, other design solutions are also possible.

The housing section 42 or the stop 43 preferably bounds the pivoting angle β of the actuating lever 26. In a variant, not shown, the stop 43 and/or the angle that is formed between the stop 43 and the longitudinal axis L or maximum pivoting angle β can be adjusted. For example, the stop 43 can occupy different predefined positions in order to individually adjust the maximum pivoting angle β for different users and/or to vary the amount of dosage. There may be different tensioned positions and/or positions of rest that are preferably adjustable or presettable. It is possible that the tensioning mechanism 28, in particular because of an altered resting position, limits a movement of the pump device 24 or the holder 25. As an alternative or in addition, the pivot arm 55 or another triggering blocker device can then be designed to block the pump device 24 and/or the holder 25 in different positions that correspond in particular to adjustable or presettable tensioned positions.

In an alternative embodiment, the pivot point 44 or the joint 31 is mounted to move relative to the actuating lever 26, for example by means of a floating bearing. In particular, the pivot point 44 or the joint 31 can be run in an advantageous way in a guide, in particular in a linear guide, in or on the actuating lever 26.

What is claimed is:

1. An inhaler, comprising:
   a respiration indicator,
   a chamber wall forming a chamber,
   a dispensing device for fluidic connection of the chamber to a nostril, and
   a discharge nozzle for forming an aerosol,
   wherein the chamber comprises an intake opening arranged for receiving the aerosol from the discharge nozzle and the dispensing device comprises an outlet from the chamber for the aerosol,
   wherein the inhaler is at least one of closed and airtight between the intake opening and the outlet,
   wherein the respiration indicator comprises a wall section extending across and airtight sealing a through passage formed in the chamber wall, wherein the wall section is flexible and configured to indicate a respiratory activity by deformation thereof, the wall section being deflectable into the chamber from a rest position of the wall section during inhalation and being deflectable outward relative to a surrounding portion of the chamber wall during exhalation, and
   wherein the chamber is formed from a dimensionally stable material apart from said wall section so as to be unresponsive to said respiratory activity except at said wall section.

2. The inhaler according to claim 1, wherein the respiration indicator reacts to the deformation of the wall section by at least one of reflection or transmission of visible light by the respiration indicator or wall section.

3. The inhaler according to claim 1, wherein the wall section has a material excess increasing inward.

4. The inhaler according to claim 1, wherein the respiration indicator is configured for indicating a pressure differential between an inside space of the chamber and an area surrounding the chamber.

5. The inhaler according to claim 1, wherein at least part of the wall section is deflectable by more than 1 mm and less than 15 mm under action of any of breathing in, out and through the chamber.

6. The inhaler according to claim 1, wherein the wall section is adapted to change from a concave curvature into a convex curvature and vice versa under the action of breathing in, out or through the chamber in a manner creating a pressure differential that acts on the wall section by more than 0.5 hPa and less than 4 hPa.

7. The inhaler according to claim 1, wherein the chamber is adapted to be placed under an underpressure under the action of breathing in and an overpressure in the chamber under the action of breathing out thereby moving or deforming the wall section.

8. The inhaler according to claim 1, wherein the wall section is connected in an opening of the chamber wall in an airtight or pressure-tight manner by at least one of having been sprayed, bonded, glued, molded, welded, clamped, or inter-engagedly locked to the chamber wall.

9. The inhaler according to claim 1, wherein the wall section has a connecting means for fastening the wall section in an opening of the chamber wall.

10. The inhaler according to claim 9, wherein the connecting means comprises a frame that forms a boundary of the wall section with a contour that corresponds to a border of the opening of the chamber wall.

11. The inhaler according to claim 1, wherein, in a position of use of the inhaler, the respiration indicator is arranged laterally or upwardly relative to a main direction of flow of breath through the chamber.

12. The inhaler according to claim 1, wherein the wall section has a surface area that is more than 0.5 cm$^2$ and less than 15 cm$^2$.

13. The inhaler according to claim 1, wherein the inhaler is at least one of closed and airtight between the intake opening and the outlet.

14. Inhaler, comprising:
   a respiration indicator,
   a chamber wall forming a chamber,
   a dispensing device for fluidic connection of the chamber to a nostril, and
   a discharge nozzle for forming an aerosol, wherein the chamber comprises an intake opening arranged for receiving the aerosol from the discharge nozzle and the dispensing device comprises an outlet from the chamber for the aerosol, wherein the respiration indicator comprises a wall section extending across and airtight sealing a through passage formed in the chamber wall, wherein the wall section is flexible and configured to indicate a respiratory activity by deformation thereof, the wall section being deflectable into the chamber from a rest position of the wall section during inhalation and being deflectable outward relative to a surrounding portion of the chamber wall during exhalation, wherein the chamber is formed from a dimensionally stable material apart from said wall section so as to be unresponsive to said respiratory activity except at said wall section, and wherein the respiration indicator reacts to the deformation of the wall section by at least one of reflection or transmission of visible light by the respiration indicator or wall section.

15. The inhaler according to claim 14, wherein the wall section has a material excess increasing inward.

16. The inhaler according to claim 14, wherein the wall section is connected in an opening of the chamber wall in an airtight or pressure-tight manner by at least one of having been sprayed, bonded, glued, molded, welded, clamped , or inter-engagedly locked to the chamber wall.

17. The inhaler according to claim 14, wherein the wall section has a connecting means for fastening the wall section in an opening of the chamber wall.

18. The inhaler according to claim 14, wherein the connecting means comprises a frame that forms a boundary of the wall section with a contour that corresponds to a border of the opening of the chamber wall.

19. Inhaler, comprising:

a respiration indicator, a chamber wall forming a chamber, a dispensing device for fluidic connection of the chamber to a nostril, and a discharge nozzle for forming an aerosol, wherein the chamber comprises an intake opening arranged for receiving the aerosol from the discharge nozzle and the dispensing device comprises an outlet from the chamber for the aerosol, wherein the respiration indicator comprises a wall section extending across and airtight sealing a through passage formed in the chamber wall, wherein the wall section is flexible and configured to indicate a respiratory activity by deformation thereof, the wall section being deflectable into the chamber from a rest position of the wall section during inhalation and being deflectable outward relative to a surrounding portion of the chamber wall during exhalation, wherein the chamber is formed from a dimensionally stable material apart from said wall section so as to be unresponsive to said respiratory activity except at said wall section, and wherein the wall section has a material excess increasing inward.

20. The inhaler according to claim 19, wherein the wall section is connected in an opening of the chamber wall in an airtight or pressure-tight manner by at least one of having been sprayed, bonded, glued, molded, welded and clamped to the chamber wall.

21. Inhaler, comprising:

a respiration indicator, a chamber wall forming a chamber, a dispensing device for fluidic connection of the chamber to a nostril, and a discharge nozzle for forming an aerosol, wherein the chamber comprises an intake opening arranged for receiving the aerosol from the discharge nozzle and the dispensing device comprises an outlet from the chamber for the aerosol, wherein the respiration indicator comprises a wall section extending across and airtight sealing a through passage formed in the chamber wall, wherein the wall section is flexible and configured to indicate a respiratory activity by deformation thereof, the wall section being deflectable into the chamber from a rest position of the wall section during inhalation and being deflectable outward relative to a surrounding portion of the chamber wall during exhalation, wherein the chamber is formed from a dimensionally stable material apart from said wall section so as to be unresponsive to said respiratory activity except at said wall section, and wherein the wall section is connected in an opening of the chamber wall in an airtight or pressure-tight manner by at least one of having been sprayed, bonded, glued, molded, welded, clamped, or inter-engagedly locked to the chamber wall.

* * * * *